Figure 1:
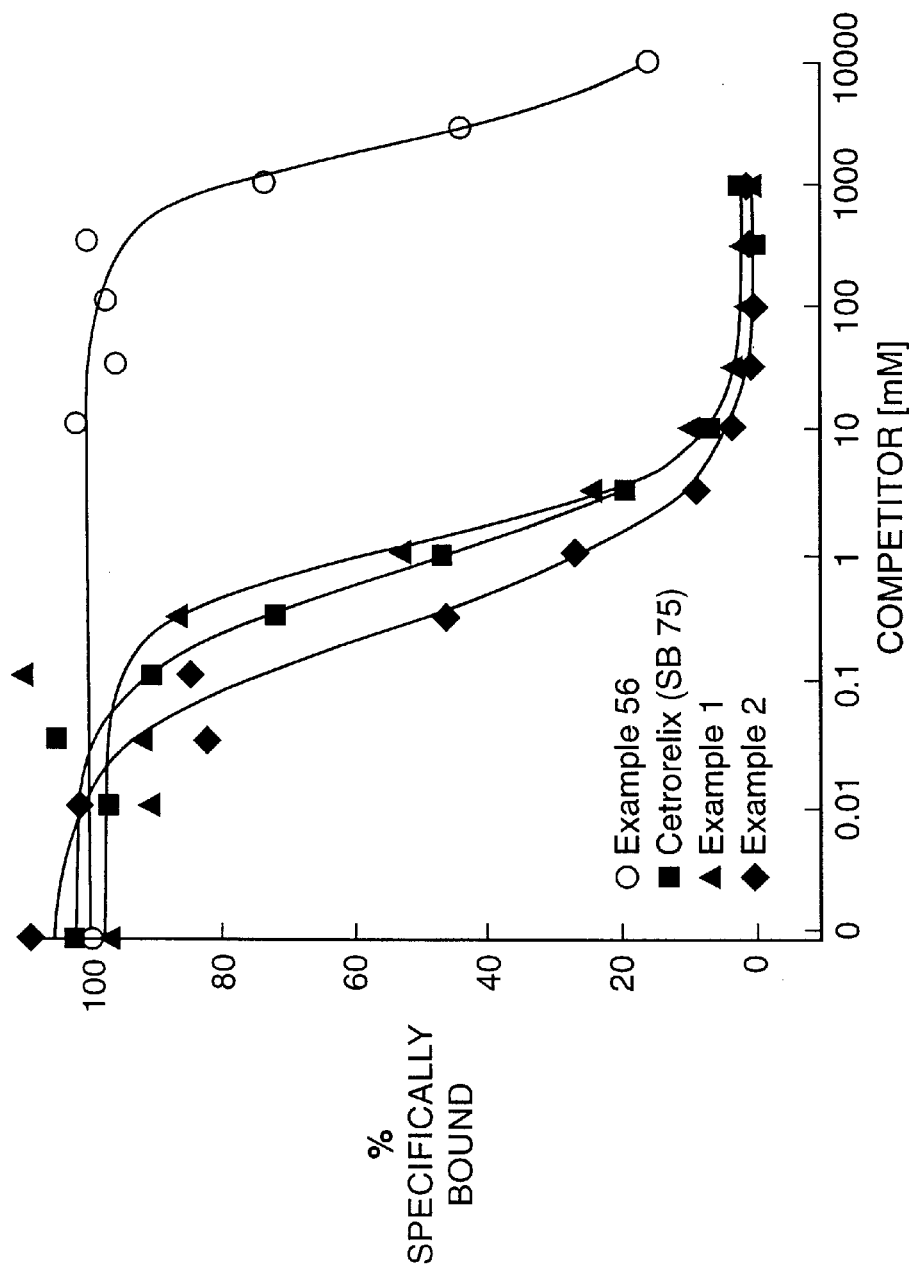

United States Patent [19]
Kutscher et al.

[11] Patent Number: 5,942,493
[45] Date of Patent: Aug. 24, 1999

[54] LH-RH ANTAGONISTS HAVING IMPROVED ACTION

[75] Inventors: Bernhard Kutscher, Maintal; Michael Bernd; Thomas Beckers, both of Frankfurt; Thomas Klenner, Ingelheim; Peter-Paul Emig, Bruchköbel; Patricia-Marie Charpentier, Maintal, all of Germany

[73] Assignee: ASTA Medica Aktiengesellschaft, Dresden, Germany

[21] Appl. No.: 09/087,274

[22] Filed: May 28, 1998

Related U.S. Application Data

[63] Continuation-in-part of application No. PCT/DE96/02171, Nov. 14, 1996.

[30] Foreign Application Priority Data

Nov. 28, 1995 [DE] Germany .......................... 195 44 212

[51] Int. Cl.$^6$ .......................... A61K 38/00; A61K 38/02; C07K 5/00; C07K 7/00

[52] U.S. Cl. .......................... 514/15; 530/300; 530/311; 530/328

[58] Field of Search .............................. 514/15; 530/300, 530/328, 311

[56] References Cited

U.S. PATENT DOCUMENTS 5,300,492   4/1994   Haviv et al. .............................. 514/15

FOREIGN PATENT DOCUMENTS 94 13313   6/1994   WIPO .

*Primary Examiner*—Avis M. Davenport
*Attorney, Agent, or Firm*—Pillsbury Madison & Sutro LLP

[57] ABSTRACT

New LH-RH antagonists are disclosed, in particular peptidomimetics and peptides modified in a side chain, their salts with pharmaceutically acceptable acids and a process for preparing these LH-RH antagonists and their salts. The disclosed peptides represent analogues of the luteinising hormone releasing hormone (LH-RH). The disclosed compounds have a high antagonistic power and are free of undesirable side effects, in particular edematogenic effects.

16 Claims, 6 Drawing Sheets

LH-RH ANTAGONISTS HAVING IMPROVED ACTION

This is a Continuation-in-Part of International Appln. No. PCT/DE96/02171 filed Nov. 14, 1996 which designated the U.S.

The invention relates to novel LH-RH antagonists, in particular peptidomimetics and peptides modified in a side chain, salts thereof with pharmaceutically acceptable acids and processes for the preparation of the LH-RH antagonists and their salts. The peptides according to the invention are analogues of the luteinizing hormone-releasing hormone (LH-RH), which has the following structure:
p-Glu-His-Trp-Ser-Tyr-Gly-Leu-Arg-Pro-Gly-NH$_2$, [LH-RH, gonadorelin].

For more than 20 years, research scientists have sought antagonists of LH-RH decapeptide with selective potency [M. Karten and J. E. Rivier, Endocrine Reviews 7, 44–66 (1986)]. The great interest in such antagonists is accounted for by their usefulness in the field of endocrinology, gynaecology, contraception and cancer. A large number of compounds have been prepared as potential LH-RH antagonists. The most interesting compounds which have been found to date are those compounds whose structure is a modification of the LH-RH structure.

The first series of potent antagonists was obtained by the introduction of aromatic amino acid esters in positions 1, 2, 3 and 6 or 2, 3 and 6. The customary manner of writing the compounds is as follows: first the amino acids are indicated which are entered in the peptide chain of LH-RH in place of the amino acids originally present, the positions in which replacement took place being marked by superscript figures. Furthermore, it is expressed by the description "LH-RH" placed afterwards that they are LH-RH analogueues in which replacement took place.

Known antagonists are:
[Ac-D-Phe(4-Cl)[1,2], D-Trp[3,6]] LH-RH (D, H. Coy et al., In: Gross, E. and Meienhofer, J. (Eds) Peptides; Proceedings of the 6th American Peptide Symposium, pp. 775–779, Pierce Chem. Co., Rockville III. (1979): [Ac-Pro[1], D-Phe (4-Cl)[2], D-Nal(2)[3,6]] LH-RH (U.S. Pat. No. 4,419,347) and [AC-Pro[1], D-Phe(4-Cl)[2], D-Trp[3,6]] LH-RH (J. L. Pineda, et al., J. Clin. Endocrinol. Metab. 56, 420, 1983).

In order to increase the water solubility of antagonists, basic amino acids, for example D-Arg, were later introduced in the 6-position. For example [Ac-D-Phe(4-Cl)[1,2], D-Trp[3], D-Arg, D-Ala[10]] LH-RH (ORG-30276) (D. H. Coy, et. al., Endocrinology 100, 1445, 1982); and
[Ac-D-Nal(2)1, D-Phe(4-F)[2], D-Trp[3], D-Arg[6]] LH-RH (ORF 18260) (J. E. Rivier et al., in: Vickery B. H. Nestor, Jr. J. J., Hafez, E. S. E. (Eds). LHRH and its Analogs, pp. 11–22 MTP Press, Lancaster, UK 1984).

Such analogues not only had the expected improved water solubility, but also showed an improved antagonistic activity. Nevertheless, these extremely potent, hydrophilic analogues with D-Arg[6] and other basic side chains in the 6-position cause temporary oedemas on the face and the extremities when they were administered subcutaneously to rats in doses of 1.25 or 1.5 mg/kg (F. Schmidt, et al., Contraception 29, 283, 1984: J. E. Morgan, et al, Int. Archs. Allergy Appl. Immun. 80, 70 (1986). Further potent LH-RH antagonists are described in WO 92/19651, WO 94/19370, WO 92/17025, WO 94/14841, WO 94/13313, U.S. Pat. Nos. 5,300,492, 5,140,009 and EP 0 413 209 A1.

The occurrence of oedematogenic effects in rats after the administration of some of these antagonists have allowed doubts to arise about their safety when used in man, and thus the introduction of these medicaments into clinical use has been delayed. There is therefore a great need for antagonistic peptides which are free of side effects.

According to the invention, the aforementioned object is achieved by compounds of the general formula (I)

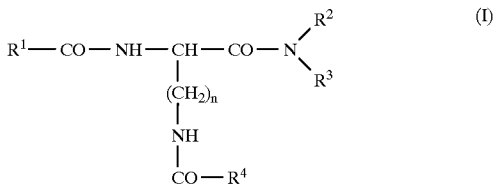

in which n is the number 3 or 4, $R^1$ is an alkyl group, an alkyloxy group, an aryl group, a heteroaryl group, an aralkyl group, a heteroaralkyl group, an aralkyloxy group or a heteroaralkyloxy group, in each case unsubstituted or substituted, $R^2$ and $R^3$ independently of one another are each a hydrogen atom, an alkyl group, an aralkyl group or a heteroaralkyl group, in each case unsubstituted or substituted, or —NR$^2$R$^3$ is an amino acid group, and $R^1$ is a group having the formula (II)

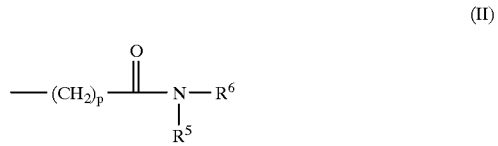

in which p is an integer from 1 to 4, $R^5$ is hydrogen or an alkyl group and $R^6$ is an unsubstituted or substituted aryl group or heteroaryl group, it being possible for the substitution, in turn, to consist of an aryl group or heteroaryl group, or $R^4$ is a ring of the general formula (III)

in which q is the number 1 or 2, $R^7$ is a hydrogen atom or an alkyl group, $R^8$ is a hydrogen atom or alkyl group and X is an oxygen or sulphur atom, where the aromatic or heteroaromatic radicals can be partially or completely hydrogenated, and chiral carbon atoms can have the R- or S-configuration, and their salts with pharmaceutically acceptable acids.

Preferred combinations of radicals $R^1$ to $R^4$ are:
a) $R^1$ is benzyloxy, $R^2$ is hydrogen and $R^3$ is hydrogen,
b) $R^1$ is benzyloxy, $R^2$ is hydrogen and $R^4$ is 4-amidinophenyl, and
c) $R^2$ is hydrogen, $R^3$ is hydrogen and $R^4$ is 4-amidinophenyl.

Preferred alkyl groups are the methl, ethyl, n-propyl, i-propyl, n-butyl, i-butyl, t-butyl, 2-ethylhexyl, dodecyl and hexadecyl groups.

Preferred aryl groups are phenyl, naphthyl, phenanthrenyl and fluorenyl groups.

Preferred heteroaryl groups are the pyridyl, pyrimidyl, imidazolyl, imidazopyridyl, indolyl, indazolyl, triazolyl, tetrazolyl, benzimidazolyl, quinolyl, 2,5-dichloropyrid-3-yl and furyl groups.

Preferred hydrogenated heteroaryl groups are the piperidino, piperazinyl, morpholino and pyrrolidinyl groups.

Aralkyl groups and heteroaralkyl groups are those groups which are bonded to the corresponding binding sites via an alkylene group, preferably a methylene, ethylene, n-propylene or n-butylene group.

Preferred substituents are halogen atoms such as fluorine, chlorine, bromine and iodine, and the methyl, ethyl, i-propyl, tert-butyl, cyano, nitro, carboxylic acid, carboxamide, carboxylic acid methyl ester, carboxylic acid ethyl ester, crotonic acid ethyl ester, trifluoromethyl, benzoyl, methoxy, benzyloxy, pyridyloxy, amino, dimethylamino, isopropylamino, amidino and quinolylmethoxy groups.

Furthermore, according to the invention, compounds of the general formula (V)

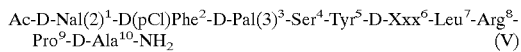

$$\text{Ac-D-Nal(2)}^1\text{-D(pCl)Phe}^2\text{-D-Pal(3)}^3\text{-Ser}^4\text{-Tyr}^5\text{-D-Xxx}^6\text{-Leu}^7\text{-Arg}^8\text{-Pro}^9\text{-D-Ala}^{10}\text{-NH}_2 \quad (V)$$

where D-Xxx is an amino acid group of the general formula (VI)

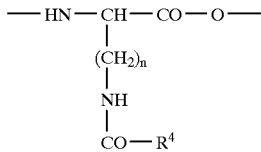

(VI)

and n, p, q, $R^4$, $R^5$, $R^6$, $R^7$, $R^8$ and X are as defined above, and their salts with pharmaceutically acceptable acids also achieve the abovementioned object.

The compounds according to the invention have a high antagonistic potency and are free of undesirable side effects, in particular free of oedematogenic effects If they are not present as salts with poorly water-soluble, pharmaceutically acceptable acids, they additionally have an improved water solubility. Furthermore, the compounds have high affinity for the human LH-RH receptor, i.e. are highly potent in inhibiting the release of gonadotropins from the pituitary gland in mammals, including man, exhibit long-lasting suppression of testosterone in rats, and cause minimal histamine release in vitro.

Preferred compounds of the general formula (I) are: α-N-Z-[ε-N'-4-(4-amidinophenyl)amino-1,4-dioxobutyl] lysinamide and α-N-Z-[ε-N'(imidazolidin-2-on-4-yl) formyl]lysinamide. Preferred peptides according to formula (V) are those in which Xxx is the [ε-N'-4-(4-imidinophenyl) amino-1,4-dioxobutyl]lysyl group or the [ε-N'-(imidazolidin-2-on-4-yl)formyl]lysyl group. The salts with pharmaceutically acceptable acids are preferably poorly soluble in water. Particularly preferred salts are those of 4,4'-methylene-bis(3-hydroxy-2-naphthoic acid), also known as embonic acid or pamoic acid.

The nomenclature used for the definition of the peptides agrees with that nomenclature explained by the IUPAC-IUB Commission on Biochemical Nomenclature (European J. Biochem. 1984, 138, 9–37), in which in agreement with the conventional representation the amino groups in the N terminus appear to the left and the carboxyl group in the C terminus appears to the right. The LH-RH antagonists such as the peptides and peptidomimetics according to the invention include amino acids occurring in nature and synthetic amino acids, the former including Ala, Val, Leu, Ile, Ser, Thr, Lys, Arg, Asp, Asn, Glu, Gin, Cys, Met, Phe, Tyr, Pro, Trp and His. The abbreviations for the individual amino acid radicals are based on the trivial names of the amino acids and are Ala alanine, Arg arginine, Gly glycine, Leu leucine, Lys lysine, Pal(3) 3-(3-pyridyl)alanine, Fal(2) 3-(2-naphthyl)alanine, Phe phenylalanine, (pCl)Phe 4-chlorophenylalanine, Pro proline, Ser serine, Thr threonine, Trp tryptophan and Tyr tyrosine. All amino acids described here originate from the L-series, if not otherwise mentioned. For example, D-Nal(2) is the abbreviation for 3-(2-naphthyl)-D-alanine and Ser is the abbreviation for L-serine. Other abbreviations used are:

| | |
|---|---|
| Boc | tert-Butyloxycarbonyl |
| Bop | Benzotriazol-1-oxytris-dimethylamino) phosphonium hexafluorophosphate |
| DCC | Dicyclohexylcarbodiimide |
| DCM | Dichloromethane |
| Ddz | Dimethoxyphenyldimethylmethylenoxycarbonyl (dimethoxydimethyl-Z) |
| DIC | Diisopropylcarbodiimide |
| DIPEA | N,N-diisopropylethylamine |
| DMF | Dimethylformamide |
| Fmoc | Fluorenylmethyloxycarbonyl |
| HF | Liquid anhydrous hydrofluoric acid |
| HOBt | 1-Hydroxybenzotriazole |
| HPLC | High-pressure liquid chromatography |
| TFA | Trifluoroacetic acid |
| Z | Benzyloxycarbonyl |

According to the invention, compounds of the general formula (I) are prepared by first providing two of the three functionalities (α-amino, ε-amino and α-carboxylic acid group) with protective groups and then reacting the free third functionality in a suitable manner. If appropriate, it is also possible, where this leads to better results, to introduce in the first step intermediate protective groups which are then replaced after the second step by the desired functionality. Suitable protective groups and methods for attaching the same are known in the field. Examples of protective groups are described in "Principles of Peptide Synthesis", Springer Verlag 1984), in the textbook "Solid Phase Peptide Synthesis" J. M. Stewart and J. D. Young, Pierce Chem. Company, Rockford, Ill. 1984, and in G. Barany and R. B. Merrifield "The Peptides", Ch. 1, pp. 1–285, 1979, Academic Press Inc.

The synthesis of compounds according to formula (IV) can be carried out both either by classical fragment condensation or by solid-phase synthesis according to Merrifield with building-up one on the other in sequence using D-lysine already acylated in the side chain by the carboxylic acid of the general formula (VII) and by reaction of a decapeptide unit with the appropriate carboxylic acids by amide linkage in the side chain of D-lysine$^6$. Accordingly, there are according to the invention three alternatives available for the process for the preparation of a compound of the general formula (V).

The first possibility comprises the steps of
(a) providing the a-amino and the carboxylic acid group of D-lysine or D-ornithine with suitable protective groups,
(b) reacting the D-lysine or D-ornithine provided with protective groups with a carboxylic acid of the general formula (VII)

$$R^4\text{—COOH} \quad (VII)$$

in which $R^4$ is as defined above,
(c) removing the protective group on the α-carboxylic acid group of the compound obtained in step (b) for the purpose of incorporation in pos. 6 in step (h), (d) coupling of D-alanine provided on the amino group with a protective group to a solid support in the form of a resin (Merrifield synthesis),
(e) removing the protective group on the amino group of the alanine,
(f) reacting the alanine bound to the solid support with proline which is provided with a protective group on the nitrogen atom,
(g) removing the protective group on the nitrogen atom of the proline,
(h) repeating steps f) and g) with the amino acids 1 to 8 according to the general formula (V), in the sequence from 8 to 1, using modified D-lysine or D-ornithine described in step (c) for pos. 6,
(i) removing the compound obtained in step (h) from the support and, if appropriate, purifying, (e.g. HPLC),
(j) if desired, reacting with a pharmaceutically acceptable acid, preferably embonic acid.

According to the second alternative, the process for the preparation of a compound of the general formula (V) comprises the steps of
(a) coupling D-alanine provided with a protective group on the amino group to a support suitable for solid-phase synthesis,
(b) removing the protective group on the amino group of the alanine,
(c) reacting the alanine bound to the resin with proline which is provided with a protective group on the nitrogen atom,
(d) removing the protective group on the nitrogen atom of the proline,
(e) repeating steps c) and d) with the amino acids 1 to 8 according to the general formula (V), in the sequence from 8 to 1,
(f) removing the compound obtained in step (e) from the support,
(g) reacting with a carboxylic acid of the formula (VII)

$$R^4\text{—COOH} \qquad (VII)$$

in which $R^4$ is as defined above,
(h) if desired, reacting with a pharmaceutically acceptable acid, preferably embonic acid.

The third variant of the process for the preparation of a compound of the general formula (V) comprises the steps of
(a) coupling D-alanine provided with a protective group on the amino group to a support suitable for solid-phase synthesis,
(b) removing the protective group on the amino group of the alanine,
(c) reacting the alanine bound to the resin with proline which is provided with a protective group on the nitrogen atom,
(d) removing the protective group on the nitrogen atom of the proline,
(e) repeating steps c) and d) with the amino acids 6 to 8 according to the general formula (V), in the sequence from 8 to 6,
(f) removing the ε-amino protective group from D-lysine or D-ornithine in pos. 6 and reacting with a carboxylic acid of the formula (VII), $$R^4\text{—COOH} \qquad (VII)$$

in which $R^4$ is as defined above,
(g) removing the protective group on the α-amino group of the D-lysine or D-ornithine,
(h) repeating steps c) and d) with the amino acids 1 to 5 according to the general formula (IV), in the sequence from 5 to 1,
(i) removing the compound obtained in step (h) from the resin and purifying it (e.g. HPLC),
(j) if desired, reacting with a pharmaceutically acceptable acid, preferably embonic acid.

Preferred carboxylic acids of the general formula (VII) are imidazolidin-2-one-4-carboxylic acid and N-(4-amidinophenyl)amino-4-oxobutyric acid.

The compounds of the formula (V) are synthesized according to the known methods, such as, for example, by pure solid-phase technique, partial solid-phase technique or by the classical solution couplings (see M. Bodanszky, "Principles of Peptide Synthesis", Springer Verlag 1984). For example, the methods of solid-phase synthesis are described in the textbook "Solid Phase Peptide Synthesisl" J. M. Stewart and J. D. Young, Pierce Chem. Company, Rockford, Ill., 1984, and in G. Barany and R. B. Merrifield "The Peptides", Ch. 1, pp. 1–285, 1979, Academic Press Inc. Classical solution syntheses are described in detail in the treatment "Methoden der Organischen Chemie [Methods of Organic Chemistry] (Houben-Weyl), Synthese von Peptiden [Peptide Synthesis]" E. Wunsch (Editor) 1974, Georg Thieme Verlag, Stuttgart, FRG.

The stepwise synthesis is carried out, for example, by first covalently binding the carboxy-terminal amino acid, whose α-amino group is protected, to an insoluble support which is customary for this purpose, removing the α-amino protective group of this amino acid, bonding the next protected amino acid to the free amino group thus obtained via its carboxyl group, and in this manner linking the other amino acids of the peptide to be synthesized step by step in the correct sequence, and after linkage of all amino acids removing the finished peptide from the support and, if appropriate, removing further side-function protective groups present. Stepwise condensation is carried out in a conventional manner by a synthesis from the appropriate amino acids protected in a customary manner. Likewise, the use of automatic peptide synthesizers, for example Labortec SP 650 type from Bachem, Switzerland, is possible using the commercially available protected amino acids.

The linkage of the individual amino acids to one another is carried out by the methods cust for this purpose, the following in particular being suitable:
Symmetric anhydrides method in the presence of dicyclohexylcarbodiimide or diisopropylcarbodiimide (DCC, DIC)
Carbodiimide method generally
Carbodiimide-hydroxybenzotriazole method
(see The Peptides, Volume 2, Ed. E. Gross and J. Meienhofer). For the linkage of arginine, the carbodiimide method is preferably used. For the other amino acids, the symmetric or mixed anhydrides method is in general used.

In the fragment coupling, acid coupling, which proceeds without racemization, or the DCC-1-hydroxybenzotriazole or DCC-3-hydroxy-4-oxo-3,4-dihydro-1,2,3-benzotriazine method is preferably used. Activated esters of fragments can also be employed.

For the stepwise condensation of amino acids, particularly highly suitable activated esters are those of N-protected amino acids, such as, for example, N-hydroxysuccinimide esters or 2,4,5-trichlorophenyl esters. The aminolysis can be catalysed very readily by N-hydroxy compounds which approximately have the acidity of acetic acid, such as, for example, 1-hydroxybenzotriazole.

Intermediate amino protective groups which are available are groups which can be removed by dehydrogenation, such as, for example, the benzyloxycarbonyl radical (=Z radical) or groups which can be removed by weak acid. Protective groups for the α-amino groups are, for example: tertiary butyloxycarbonyl groups, carbobenzoxy groups or carbobenzothio groups (if appropriate in each case having a p-bromo or p-nitrobenzyl radical), the trifluoroacetyl group, the phthalyl radical, the o-nitrophenoxyacetyl group, the trityl group, the p-toluenesulphonyl group, the benzyl group, benzyl radicals substituted in the benzene nucleus (p-bromo or p-nitrobenzyl radical) and the α-phenylethyl radical. Reference is also made here to the book by Jesse P. Greenstein and Milton Winitz, Chemistry of Amino Acids, New York 1961, John Wiley and Sons, Inc., Volume 2, for example page 883 et seq. and The Peptides, Volume 2, Ed. E. Gross and J. Meienhofer, Academic Press, New York, These protective groups are fundamentally also suitable for the protection of further functional side groups (OH groups, $NH_2$ groups) of the corresponding amino acids.

Hydroxyl groups present (serine, threonine) are preferably protected by benzyl groups and similar groups. Further amino groups not in the α-position (for example amino groups in the ω-position, the guanidino group of arginine) are preferably protected orthogonally.

The reaction for the linkage of amino acids takes place in a customary indifferent solvent or suspending agent therefor (for example dichloromethane), it being possible to add dimethylformamide, if necessary, to improve the solubility.

For introduction of the $R^4$—CO group by reaction of the amino group of the lysine with the carboxylic acid of the general formula (VII), fundamentally the same processes as described above are suitable for linkage of the amino acids. Particularly preferred, however, is condensation using carbodiimide, for example 1-ethyl-3-(3-dimethylaminopropyl)carbodiimide, and 1-hydroxybenzotriazole.

Suitable synthetic supports are insoluble polymers, for example polystyrene resin in bead form, which can be swollen in organic solvents (for example a copolymer of polystyrene and 1% divinylbenzene). The synthesis of a protected decapeptide amide on a methylbenzhydrylamide resin (MBHA resin, i.e. polystyrene resin provided with methylbenzhydrylamide groups) which affords the desired C-terminal amide function of the peptide after an HF cleavage from the support can be carried out according to the following flow diagram:

Flow diagram
Peptide synthesis protocol

| Stage | Function | Solvent/reagent (v/v) | Time |
|---|---|---|---|
| 1 | Washing | Methanol | 2 × 2 min |
| 2 | Washing | DCM | 3 × 3 min |
| 3 | Removal | DCM/TFA (1:1) | 1 × 30 min |
| 4 | Washing | Isopropanol | 2 × 2 min |
| 5 | Washing | Methanol | 2 × 2 min |
| 6 | Washing | DCM | 2 × 3 min |
| 7 | Neutralization | DCM/DIPEA (9:1) | 3 × 5 min |
| 8 | Washing | Methanol | 2 × 2 min |
| 9 | Washing | DCM | 3 × 3 min |
| 10 | STOP | Addition of the Boc-As in DCM + DIC + HOBt | |
| 11 | Coupling | — | about 90 min |
| 12 | Washing | Methanol | 3 × 2 min |
| 13 | Washing | DCM | 2 × 3 min |

The Nα-Boc-protected amino acids are coupled in a three-fold molar excess in the presence of diisopropylcarbodiimide (DIC) and 1-hydroxybenzotriazole (HOBt) in $CH_2Cl_2$/DMF in the course of 90 mine and the BOC protective group is removed by action of 50% trifluoroacetic acid (TFA) in $CH_2Cl_2$ for half an hour. To check for complete conversion, the chloranil test according to Christensen and the Kaiser's ninhydrin test can be used. Radicals of free amino function are blocked by acetylation in a five-fold excess of acetylimidazole in $CH_2Cl_2$. The sequence of the reaction steps of peptide synthesis on the resin follows from the flow diagram. For the removal of the resin-bound peptides, the respective final product of solid-phase synthesis is dried in vacuo over $P_2O_5$ and treated at 0° C. for 60 min in a 500-fold excess of HF/anisole 10:1 (v:v).

After distilling off HF and anisole in vacuo, the peptide amides are obtained by stirring with anhydrous ethyl ether as white solids; the removal of polymeric Support additionally obtained is carried out by washing with 50% strength aqueous acetic acid. By careful concentration of the acetic acid solutions in vacuo, the respective peptides can be obtained as highly viscous oils, which are converted into white solids in the cold after addition of abs. ether.

Further purification is carried out by routine methods of preparative high-pressure liquid chromatography (HPLC).

The conversion of the peptides into their acid addition salts can be effected by reaction thereof with acids in a manner known per se. Conversely, free peptides can be obtained by reaction of their acid addition salts with bases. Peptide embonates can be prepared by reaction of trifluoroacetic acid salts (TFA salts) of the peptide with free embonic acid (pamoic acid) or the corresponding disodium salt of embonic acid. To do this, the peptide TFA salt is treated in aqueous solution with the solution of disodium embonate in polar aprotic medium, preferably dimethylacetamide, and the pale yellow precipitate formed is isolated.

The following examples illustrate the invention without limiting it.

EXAMPLE 1

Ac-D-Nal(2)-D(pCl)Phe-D-Pal(3)-Ser-Tyr-D-[ε-N'-(imidazolidin-2-on-4-yl)formyl]-Lys-Leu-Arg-Pro-D-Ala-$NH_2$ The synthesis was carried out according to the flow diagram on 5 g of mBHA resin (loading density 1.08 mmol/g). Lysine was coupled as Fmoc-D-Lys(Boc)-OH and acylated with imidazolidin-2-one-4-carboxylic acid in a 3-fold excess after removal of the Boc group in the side chain. After removal of the Fmoc protective group with 20% piperidine/DMF, extension was carried out at the N terminus according to the flow diagram. After removal of the polymeric support, 5.2 g of crude peptide were obtained, which were purified by standard processes of preparative HPLC. After subsequent freeze drying, 2.1 g of HPLC-homogeneous product of the empirical formula $C_{74}H_{97}N_{18}O_{15}Cl$ having the correct FAB-MS 1514 (M+H$^+$) (calc. 1512.7) and corresponding $^1$H-NMR spectrum were obtained.

$^1$H-NMR (500 MHz, DMSO-$d_6$, δ in ppm): 8.56, m, 2H, arom. H; 8.08, m, 1H, arom. H; 7.81, m, 1H, arom. H; 7.73 m, 2H, arom. H; 7.66, m, 1H, arom. H; 7.60, s, 1H, arom. H; 7.44, m, 2H, arom. H; 7.30, d, 1H, arom. H; 7.25, and 7.18, 2d, 2×2H, arom. H p-Cl-Phe; 6.97 and 6.60, 2d, 2×2H, arom. H Tyr; 9.2–6.3, several signals, amide NH; 4.8–4.0, several m, Cα-H and aliph. H; 2.1–1.1, several m, residual aliphat. H; 1.70, s, 3H, acetyl; 1.22, d, 3H, Cβ-H Ala; 0.85, dd, 6H, Cδ-H Leu

EXAMPLE 2

Ac-D-Nal(2)-D(pCl)Phe-D-Pal(3)-Ser-Tyr-D-[ε-N'-4-(4-amidinophenyl)amino-1,4-dioxobutyl]-Lys-Leu-Arg-Pro-D-Ala-$NH_2$ 0.7 mmol (1.03 g) of decapeptide Ac-D-Nal-D-(pCl)Phe-D-Pal-Ser-Tyr-D-Lys-Leu-Arg-Pro-D-Ala-NH$_2$ was reacted with 1.0 mmol (0.27 g) of (4-amidinophenyl)amino-4-oxobutyric acid in the presence of 1.0 mmol (0.16 g) of 1-ethyl-3-(3-dimethylaminopropyl)carbodiimide and 1.0 mmol (0.16 g) of 1-hydroxybenzotriazole in freshly distilled DMF. The solvent was removed after 24 h in vacuo, the residue obtained was dissolved in water and the solution was freeze dried. The crude reaction product obtained (1.63 g) was purified by preparative reverse-phase HPLC; altogether 0.61 g of HPLC-homogeneous product of empirical formula $C_{81}H_{104}N_{19}O_{15}Cl$ having the correct FAB-MS: 1618.7 (M+H$^+$) (calc. 1617.7) and corresponding $^1$H-NMR spectrum were obtained.

$^1$H-NMR (500 MHz, DMSO-d$_6$, δ in ppm): 10.4, s, 1H and 9.15, s, 2H, and 8.8, s, 1H, NH's of 4-amidinoaniline; 8.60, m, 2H, arom. H; 8.20, m, 1H, arom. H; 7.80, m, 1H, arom. H; 7.73, m, arom. H; 7.61, s, 1H, arom. H; 7.44, m, 2H, arom. H; 7.30, d, 1H, arom. H; 7.25 and 7.20, 2d, 4H, arom. H (pCl)Phe; 7.0 and 6.6, 2D, 4H, arom. H Tyr; 8.3–7.2; several signals, amide-NH; 4.73–4.2, several multiplets, Cα-H; 4.13, m, 1H, Cα-H; Ala; 3.78–2.4, several multiplets, Cβ-H and aliphat. H; 1.72, s, 3H, acetyl; 1.22, d, 3H, Cβ Ala; 0.85, dd, 6H, Cδ Leu

EXAMPLE 3

0.5 g (0.3 mmol) of peptide LH-RH antagonist according to Example 1, dissolved in 50 ml of H$_2$O, was converted by reaction with 0.130 g (0.3 mmol) of disodium pamoate in 2 ml of aqueous solution to peptide embonate, which rapidly deposited from the solution as a yellow precipitate. 0.281 g of finely crystalline yellow-green powder were obtained, embonic acid content 33%.

EXAMPLE 4

0.3 g (0.17 mmol) of peptide LH-RH antagonist according to Example 2, dissolved in 5 ml of dimethylacetamide, was converted by reaction with 0.195 g (0.45 mmol) of disodium pamoate in 2 ml of aqueous solution to peptide embonate, which after addition of 50 ml of H$_2$O was obtained as a yellow precipitate. 0.330 g of finely crystalline yellow product were obtained, embonic acid content 20%.

Compounds of the general formula I are obtainable according to the following Schemes 1, 3, 4 and 5, the three functionalities R$^1$, R$^3$ and R$^4$ being varied systematically. Scheme 1 shows the synthesis of the compound of Example 1:

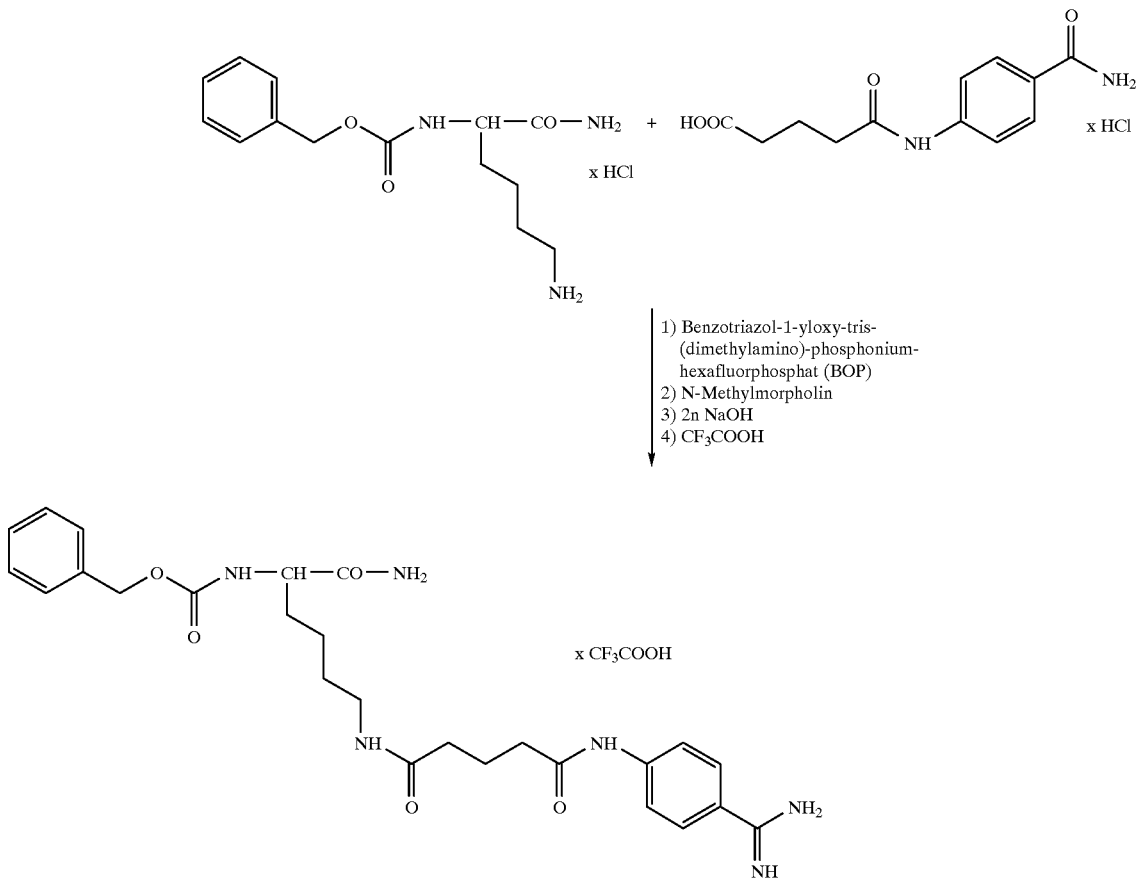

Scheme 1

1) Benzotriazol-1-yloxy-tris-(dimethylamino)-phosphonium-hexafluorphosphat (BOP)
2) N-Methylmorpholin
3) 2n NaOH
4) CF$_3$COOH General Procedure for the preparation of the compounds of the general formula I according to Scheme 1

The carboxylic acid R$^4$—COOH substituted by the radical R$^4$, on which the general formula I and the Synthesis Scheme 1 are based, which in the case of a basic radical for R$^4$ can also be present as a salt, for example as a hydrochloride, hydrosulphate or acetate, is dissolved or suspended with exclusion of moisture and with stirring in a non-polar or dipolar aprotic organic solvent, such as, for example, tetrahydrofuran, dioxane, methyl tert-butyl ether, tolulene, dimethylformamide, dimethylacetamide, N-methylpyrrolidone, dimethyl sulphoxide or methylene chloride and treated with stirring with a base serving as an acid trap, such as, for example, with diisopropylamine, triethylamine, N-methylmorpholine, dimethylaminopyridine or pyridine. A mixture of Z-(L)-lysinamide hydrochloride in a diduent is then added, a suitable diduent being that employed above for dissolving the carboxylic acid $R_4$—COOH substituted by the radical $R_4$. The pH of the reaction mixture is then adjusted using one of the bases employed as an acid trap, for example, to pH 6.5–9.0, preferably to 7.0–8.5, particularly to 7.0–7.5. Finally, the solution of a coupling reagent, e.g. benzotriazol-1-yloxy-tris (dimethylamino)phosphonium hexafluorophosphate (BOP), or benzotriazol-1-yloxy-tripyrrolidinophosphonium hexafluorophosphate (PyBOP) or dicyclohexylcarbodiimide (DCC) is added to the reaction mixture with further stirring and the pH of the solution is adjusted again to the above-mentioned pH range after a short time. The suspension is stirred, for example, at 0–80° C., preferably at 10–50° C., particularly at 20–30° C., for 1–15 hours, then filtered off with suction, the solid is washed and the filtrate is concentrated to dryness in vacuo. The residue is crystallized by rubbing with an organic solvent, for example with toluene, tetrahydrofuran, acetone, methyl ethyl ketone or isopropyl alcohol or it is purified by recrystallization, distillation or by column or flash chromatography on silica gel or alumina. The eluent used, is, for example, a mixture of methylene chloride, methanol, ammonia (25%) in the ratio 85:15:1 (vol/vol) or a mixture of methylene chloride, methanol, ammonia (25%) in the ratio 80:25:5 (vol/vol).

Trifluoroacetate Synthesis:

The compound purified according to the procedure described above is dissolved in protic or aprotic solvents, e.g. in alcohols, such as methanol, EtOH, isopropanol, or in cyclic ethers, such as, for example, tetrahydrofuran or dioxane, and adjusted to a pH of 10–11 using 2N sodium hydroxide solution. The solid precipitated is filtered off with suction, washed, dried in vacuo and treated in ethanolic solution at a temperature of 10–80° C., preferably 20–40° C., with a molar equivalent or 2–4 fold molar excess of trifluoroacetic acid. After standing of the solution at 0–4° C. for 24 hours the desired trifluoroacetate crystallizes, which is filtered off with suction and dried in vacuo.

According to this general procedure, on which Synthesis Scheme 1 is based, compounds were synthesized which follow below from the description of Example 5 and the following Table 1:

EXAMPLE 5

α-N-[Benzyloxycarbonyl]-ε-N-[5-[(4-amidino-phenyl) amino]-5-oxo-pentanoyl]-L-lysinamide trifluoroacetate 5 g (17.5 mmol) of 5-[[4-(aminoiminomethyl)phenyl] amino]-5-oxopentanoic acid hydrochloride are suspended with stirring and exclusion of moisture in 200 ml of dimethylformamide and treated with 3.85 ml (35.0 mmol) of N-methylmorpholine. A mixture of 5.53 g (17.5 mmol) of Z-(L)-lysinamide hydrochloride in 100 ml of dimethylformamide is added and the pH is adjusted to 7.0–7.5 using N-methylmorpholine. Finally, a solution of 9.73 g (21.9 mmol) of benzotriazol-1-yloxy-tris(dimethylamino) phosphonium hexafluorophosphate (BOP) is added and after 10–15 minutes the pH is again adjusted to 7.0–7.5. The yellow-coloured suspension is stirred with continuous checking of the pH, which should be 7.0–7.5, for 3–4 hours at room temperature, the colourless precipitate is filtered off with suction, washed twice with dimethylformamide and the yellow-coloured filtrate is evaporated to dryness. The oily residue is digested with a total of 5×40 ml of methyl ethyl ketone in such a way that after each of the 5 solvent treatments the methyl ethyl ketone phase is poured off and discarded. The residual crude product, which is obtained in crystalline form, is filtered off with suction, washed with 30 ml of methyl ethyl ketone and dried at room temperature in vacuo. The solid is then dissolved in about 50 ml of ethanol and adjusted to pH 10–11 using 2N sodium hydroxide solution. The precipitated base is filtered off with suction, washed with water and ethanol and dried at 35° C. in vacuo.

Yield: 5.5 g (62% of theory)

Trifluoroacetate: 5.5 g of base are treated at 60° C. in ethanolic suspension with a 5-fold molar amount of trifluoroacetic acid. The solution is stored overnight at 4° C., and the trifluoroacetate obtained is filtered off with suction and dried at 35° C. in vacuo.

Yield: 5.9 g (87.7% theory)

Melting point: 185° C.

| Elemental analysis: | | | | | | |
|---|---|---|---|---|---|---|
| calc. | C | 53.84 | H | 5.65 | N | 13.45 |
| found | C | 54.11 | H | 5.74 | N | 13.33 |

$^1$H-NMR (500 Mhz DMSO-$d_6$, δ in ppm):

10.47, s, 1H, anilide, 9.14 and 8.8 2s, NH amidine, 7.82, m, 1H, lys-ε-NH, 7.79 and 7.46, 2s, aromat. H, 7.27 and 6.93 2s, 2H, CONH$_2$, 7.20, d, 1H, urethane NH, 5.0, s, 2H, benzyl H, 3.89, m, 1H, Cα-H, 3.0 and 2.58 and 2.40, 3 m, altogether 6H, aliphat. H, 1.60–1.20, 4 m, altogether 6H, rem. Aliphat. H (Formula I)

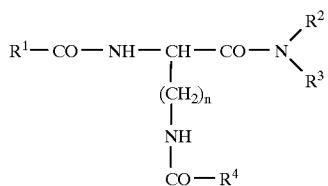

According to the above procedure further compounds shown in Table I below were prepared, n being equal to 4 throughout.

TABLE 1

α,ε-N-substituted L-lysinamide derivatives
according to Synthesis Scheme 1 and to the
general formula I (for all Examples n is equal to 4)

| Example | R¹—CO | R²/R³ | R⁴ |
|---|---|---|---|
| 5 Trifluoroacetate | benzyloxycarbonyl (PhCH₂-O-C(=O)-) | H/H | -CH₂CH₂-C(=O)-NH-C₆H₄-C(=NH)NH₂ (para) |
| 6 | | | -CH₂CH₂-C(=O)-NH-C₆H₄-CN (para) |
| 7 | | | -CH₂CH₂-C(=O)-NH-C₆H₄-F (para) |
| 8 | | | -CH₂CH₂-C(=O)-NH-C₆H₄-Cl (para) |
| 9 | | | -CH₂CH₂-C(=O)-NH-C₆H₄-Br (para) |
| 10 | | | -CH₂CH₂-C(=O)-NH-C₆H₄-CH(CH₃)₂ (para) |
| 11 | | | -CH₂CH₂-C(=O)-NH-C₆H₄-C(CH₃)₃ (para) |
| 12 | | | -CH₂CH₂-C(=O)-NH-C₆H₅ |
| 13 | | | -CH₂CH₂-C(=O)-NH-C₆H₄-OBzl (para); OBzl = Benzyloxy |

TABLE 1-continued
α,ε-N-substituted L-lysinamide derivatives
according to Synthesis Scheme 1 and to the
general formula I (for all Examples n is equal to 4)
| Example | R¹—CO | R²/R³ | R⁴ |
|---|---|---|---|
| 14 | | | 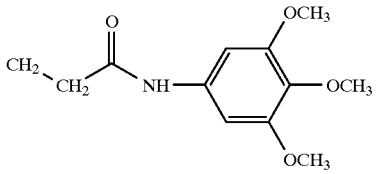 |
| 15 | | | 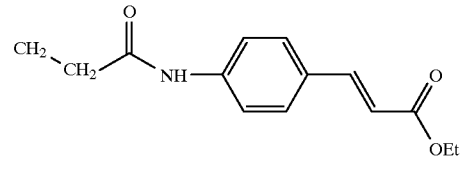 |
| 16 | 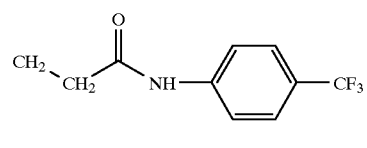 | H/H | 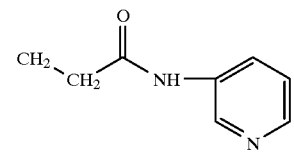 |
| 17 | | | 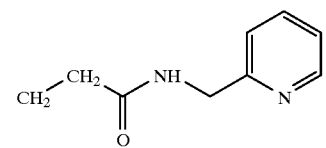 |
| 18 | | | 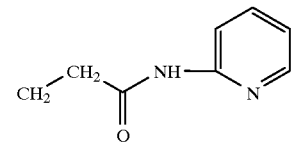 |
| 19 | | | 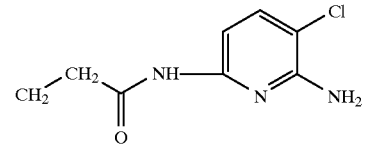 |
| 20 | | | 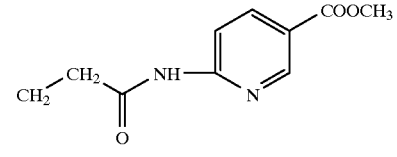 |
| 21 | | |  |

TABLE 1-continued

α,ε-N-substituted L-lysinamide derivatives
according to Synthesis Scheme 1 and to the
general formula I (for all Examples n is equal to 4)

| Example | R¹—CO | R²/R³ | R⁴ |
|---|---|---|---|
| 22 | | | (CH₂-CH₂-C(O)-NH-pyrimidin-2-yl) |
| 23 | | | (CH₂-CH₂-C(O)-NH-(6-aminopyridin-2-yl)) |
| 24 | | | (CH₂-CH₂-C(O)-NH-[2-amino-6-(4-fluorobenzylamino)pyridin-3-yl]) |
| 25 | benzyloxycarbonyl (Cbz) | H/H | (CH₂-CH₂-C(O)-NH-biphenyl-4-yl) |
| 26 | | | (CH₂-CH₂-C(O)-NH-[4-(pyridin-3-yloxy)phenyl]) |
| 27 | | | (CH₂-CH₂-C(O)-NH-[3-methyl-4-((2,6-dichloropyridin-3-yl)methyl)phenyl]) |
| 28 | | | (CH₂-CH₂-C(O)-NH-[2-(ethoxycarbonyl)imidazo[1,2-a]pyridin-8-yl]) |

TABLE 1-continued

α,ε-N-substituted L-lysinamide derivatives
according to Synthesis Scheme 1 and to the
general formula I (for all Examples n is equal to 4)

| Example | R¹—CO | R²/R³ | R⁴ |
|---|---|---|---|
| 29 | | | 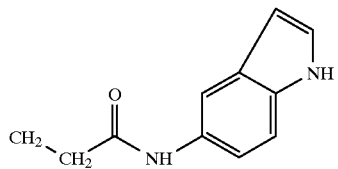 |
| 30 | | | 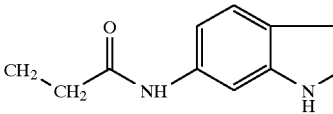 |
| 31 | | | 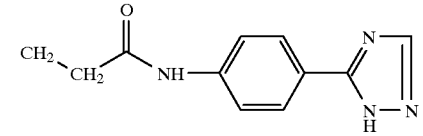 |
| 32 | | | 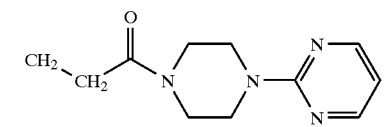 |
| 33 | | | 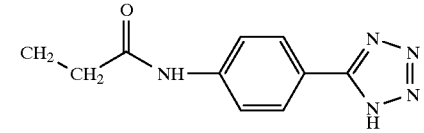 |
| 34 | | | 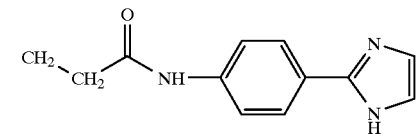 |

The melting points of the compounds according to the above examples can be seen from Table 2 below:

TABLE 2

Melting points of the compounds according to Examples 5 to 34

| Example | m.p. [°C.] |
|---|---|
| 5 | 185 |
| 6 | 185 |
| 7 | 216–220 |
| 8 | 225 |
| 9 | 217–220 |
| 10 | 218–222 |
| 11 | 208–212 |
| 12 | (oil) |
| 13 | 232–236 |
| 14 | 194–198 |
| 15 | 225 |
| 16 | 211–214 |

TABLE 2-continued

Melting points of the compounds according to Examples 5 to 34

| Example | m.p. [°C.] |
|---|---|
| 17 | 183–186 |
| 18 | (oil) |
| 19 | syrupy residue |
| 20 | (oil) |
| 21 | (oil) |
| 22 | (oil) |
| 23 | syrupy residue |
| 24 | (oil) |
| 25 | syrupy residue |
| 26 | 205–210 |
| 27 | 172–177 |
| 28 | 227–230 |

TABLE 2-continued

Melting points of the compounds according to Examples 5 to 34

| Example | m.p. [°C.] |
|---|---|
| 29 | 225–229 |
| 30 | 233–235 |
| 31 | 215–218 |
| 32 | 155 |
| 33 | (oil) |
| 34 | (oil) |

Precursors for the compounds of the general formula I prepared according to Synthesis Scheme 1, which follow from Table 1

The Z-(L)lysinamide employed as a starting compound for the synthesis final stage of Examples 5–34 is commercially available. The substituted "aryl"- or "heteroarlyamino-oxo-alkanoic acids" used as further starting materials and following from synthesis Scheme 1 can be prepared by procedures known from the literature analogueously to Synthesis Scheme 2 (P. R. Bovy, J. Organ. Chem. 58, 7948 (1993)).

Scheme 2

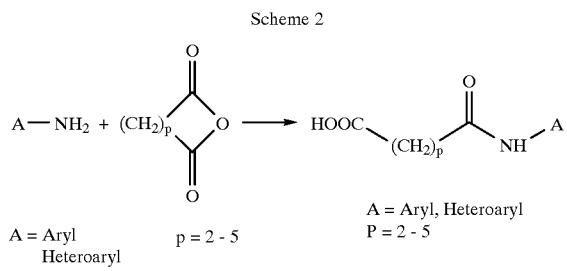

The aromatic or heteroaromatic amines A—NH$_2$ used, which follow from Synthesis Scheme 2, are commercially available; the aminoimidazo[1,2-a]pyridine on which the compound of Example 28 is based can be synthesized analogueously to procedures known from the literature (R. Westwood, J. Med. Chem 31, 1098 (1988)).

The "aryl"- or "heteroarylamino-oxo-alkanoic acids" already predesignated as precursors can furthermore be prepared by, starting from a monomethyl alkane-dicarboxylate, e.g. monomethyl suberate and monomethyl azelate, reacting with an aromatic or heteroaromatic amine by means of an aminolysis reaction in a boiling alcohol, for example in boiling ethanol or butanol, or optionally in an aromatic solvent, such as, for example, in toluene or xylene, at boiling heat, optionally in an autoclave at the boiling point of the solvent using a pressure of up to 50 bar, concentrating the reaction solution in vacuo and purifying the residue by crystallization from methanol or ethanol or by column chromatography. The eluent used is, for example, a mixture of methylene chloride, methanol, ammonia (25%) in the ratio 85:15:1 (vol/vol) or a mixture of methylene chloride, methanol, ammonia (25%) in the ratio 80:25:5 (vol/vol).

An alternative course of the process for the preparation of compounds of the general formula (I), in which R$^1$ is the benzyloxycarbonyl group and R$^2$ and R$^3$ are a hydrogen atom, is as follows:

1. The α-carboxylic acid group is amidated.
2. The ε-amino group is protected with the Z group.
3. The α-amino group is protected with the Boc group such that a selectivity with respect to the later removal of the amino protective groups results.
4. The Z group on the ε-amino group is removed.
5. The desired group R$^4$—CO— is introduced on to the ε-amino group.
6. The Boc group on the α-amino group is removed.
7. The α-amino group is provided with the Z group.

Further compounds of the general Formula I are obtainable according to the following Scheme 3, representing the synthesis of the compound of Example 35:

Scheme 3

1. Stufe

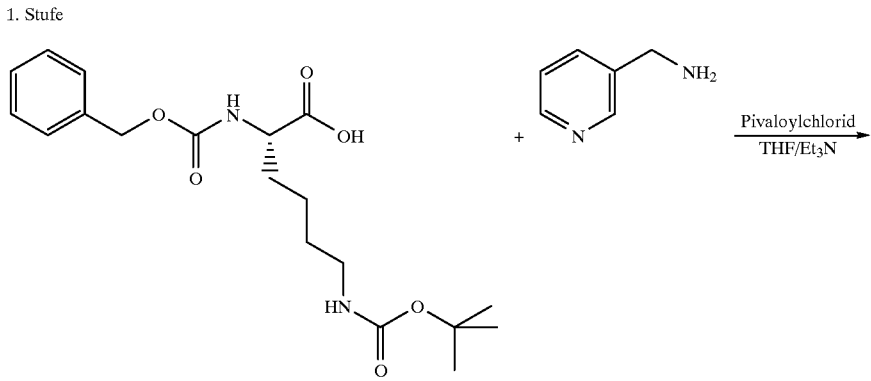

2. Stufe

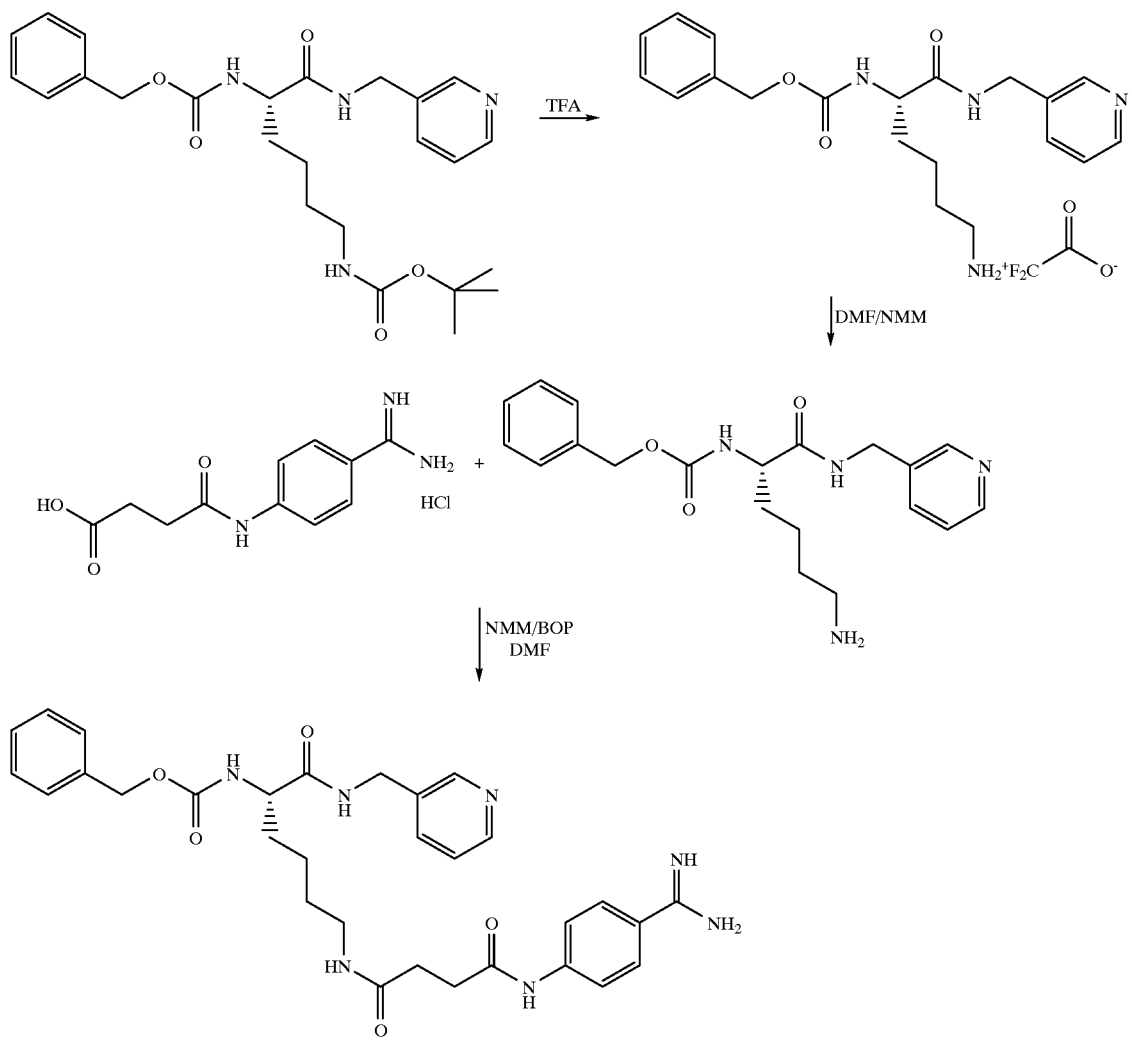

General procedure for the preparation of the compounds of the general formula I according to Scheme 3:

1st Stage

Z-Lys(BOC)-OH and a base, for example triethylamine, diisopropylamine, N-methylmorpholine, N-ethylpiperidine, and an aliphatic or aromatic carbonyl chloride, for example acetyl chloride, isobutyroyl chloride, isovaleroyl chloride, pivaloyl chloride, benzoyl chloride or 4-methoxybenzoyl chloride are added at a temperature within a range from −30° C. to 30° C., preferably between −20° C. to 20° C., particularly between −15° C. and 5° C., to a dipolar aprotic or non-polar organic solvent, such as, for example, tetrahydrofuran, dimethyl sulphoxide, dimethyl-formamide, acetonitrile, ethyl acetate, dimethyl-acetamide, N-methylpyrrolidone, dioxane, toluene, ether, methylene chloride or chloroform. After some time, for example 30 minutes to 3 hours, a solution or suspension, cooled to −10° C., of an amine in a dipolar aprotic or non-polar organic solvent, for example tetrahydrofuran, dimethyl sulphoxide, dimethylformamide, acetonitrile, ethyl acetate, dimethylacetamide, N-methylpyrrolidone, dioxane, toluene, ether, methylene chloride or chloroform, is added with vigorous stirring. The suspension is stirred at a temperature within a range from −30° C. to 30° C., preferably between −20° C. and 20° C., particularly between −15° C. and 5° C., for 1 to 2 hours. After ending of the reaction, the base is filtered off with suction as the hydrochloride and the solvent is concentrated. The oily residue is treated with an aprotic or non-polar organic solvent, for example ether, diisopropyl ether, methyl tert-butyl ether, petroleum ether, toluene, xylene, pentane, hexane. The solution is stirred for some time, for example 30 minutes to 3 hours, until a white powder is precipitated. The precipitate is filtered off with suction and dried.

2nd Stage

The Z-Lys(Boc)amide obtained according to the above procedure of the 1st Stage is dissolved in trifluoroacetic acid at a temperature between −20° C. and 30° C., preferably between −10° C. and 20° C., particularly between −5° C. and 5° C. and stirred for a period of 15 minutes to 1 hour. The excess trifluoroacetic acid is concentrated and the oily residue is treated with a dipolar aprotic or non-polar organic solvent, such as, for example, dimethylformamide, methylene chloride, tetrahydrofuran, acetonitrile, N-methylpyrrolidone, ethyl acetate. The desired acid, a base, such as, for example, diisopropylethylamine, N-methylmorpholine and the suitable coupling reagent such as, for example, BOP, PyBOP, DCC are then added in a dipolar aprotic or non-polar organic solvent, such as, for example, dimethylformamide, methylene chloride, tetrahydrofuran, acetonitrile, N-methylpyrrolidone, ethyl acetate. The reaction takes place at a temperature from −10° C. to 100° C., preferably at 0° C. to 80° C., particularly between 10° C. and 35° C. After a reaction time of 1 to 5 hours and standing at room temperature for 24 hours, the solvent is concentrated. The residue is precipitated using an organic solvent, such as, for example, water, isopropanol, methylene chloride or ether. The crude product is purified by chromatography on a silica gel column.

According to this general procedure for Stages 1 and 2, on which the Synthesis Scheme 3 is based, compounds were synthesized which follow from Table 3 below, n being equal to 4 throughout.

TABLE 3

$$R^1-CO-NH-CH(-( CH_2)_n-NH-CO-R^4)-CO-N(R^2)(R^3)$$

(Formula I)

α,ε-N-substituted L-lysinamide derivatives according to synthesis Scheme 3 and the general formula I (for all Examples n is equal to 4)

| Example | R¹—CO | R² | R³ | R⁴ |
|---|---|---|---|---|
| 35 | benzyl-O-C(=O)— | H | CH₂-(3-pyridyl) | CH₂-C(=O)-NH-(4-amidinophenyl) |
| 36 |  |  | CH₂-(2-pyridyl) |  |
| 37 |  |  | CH₂-phenyl |  |
| 38 |  |  | CH₂-(2,4-dimethoxyphenyl) |  |
| 39 | benzyl-O-C(=O)— | H | CH₂-(3,4-dimethoxyphenyl) | CH₂-C(=O)-NH-(4-amidinophenyl) |

TABLE 3-continued $$R^1-CO-NH-CH(-(CH_2)_n-NH-CO-R^4)-CO-N(R^2)(R^3)$$

(Formula I)

α,ε-N-substituted L-lysinamide derivatives according to synthesis Scheme 3 and the general formula I (for all Examples n is equal to 4)

| Example | R¹—CO | R² | R³ | R⁴ |
|---|---|---|---|---|
| 40 | | | (S)-CH(CH₃)-C(=O)-NH₂ | |
| 41 | | | CH₂-C₆H₄-NH₂ (para) | |
| 42 | | | CH₂-(2-furyl) | |
| 43 | | | CH₂-(4-pyridyl) | |
| 44 | | | CH₂-(2-pyridyl) | |
| 45 | | | CH₂-C₆H₄-OCH₃ (ortho) | |
| 46 | | | CH₂-CH₂-N(CH₃)₂ | |
| 47 | | | CH₂-CH₂-(1-imidazolyl) | |

TABLE 3-continued
$$R^1\text{—CO—NH—CH—CO—N}\genfrac{}{}{0pt}{}{R^2}{R^3}$$
$$|$$
$$(CH_2)_n$$
$$|$$
$$NH$$
$$|$$
$$CO\text{—}R^4$$
(Formula I)
α,ε-N-substituted L-lysinamide derivatives according to synthesis Scheme 3 and the general formula I (for all Examples n is equal to 4)
| Example | R¹—CO | R² | R³ | R⁴ |
|---------|-------|----|----|----|
| 48 | | | 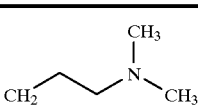 | |
| 49 | 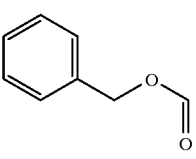 | H | 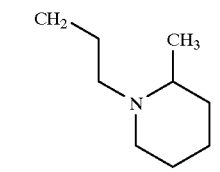 | 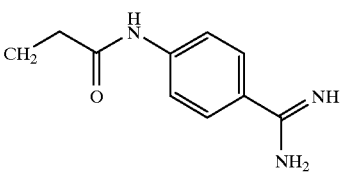 |
| 50 | | | 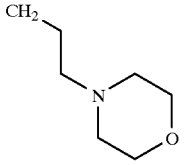 | |
| 51 | | | 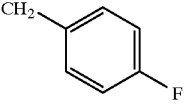 | |
| 52 | | | 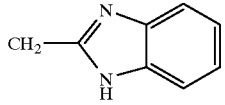 | |
| 53 | | | 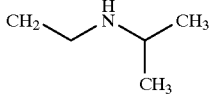 | |
| 54 | | | 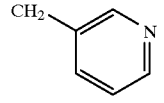 | |
| 55 | | | 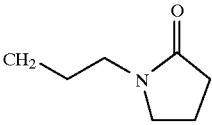 | |

EXAMPLE 35

N-(α-N-Z-[ε-N-4-(4-Amidinophenyl)-amino-1,4-dioxobutyl]lysine-N-(3-pyridylmethyl))amide 1st Stage Z-Lys(Boc)-N-(3-pyridylmethyl)amide N-(α-N-Z-[ε-N-tert-butyloxycarbonyl]lysine-N-(3-pyridylmethyl)amide 4 g (10 mmol) of Z-Lys(Boc)-OH, which is commercially available, 1 g (10 mmol) of triethylamine and 1.26 g (10 mmol) of pivaloyl chloride are added at −15° C. to 60 ml of tetrahydrofuran. After 30 minutes, a solution, precooled to −10° C., of 1.08 g (10 mmol) of 3-(aminomethyl)pyridine in 20 ml of tetrahydrofuran is added with vigorous stirring. The suspension is stirred at −15° C. for 1 to 2 hours. The triethylamine hydrochloride is filtered off with suction at low temperature and the tetrahydrofuran is then evaporated. The oily residue is treated with 100 ml of diethyl ether. The solution is stirred until a white powder precipitates. The precipitate is filtered off with suction and dried. Yield: 4 g (85% of theory).

2nd Stage

N-(α-N-Z-[ε-N-4-(4-Amidinophenyl)-amino-1,4-dioxobutyl]lysine-N-(3-pyridylmethyl)amide 2 g (4.25 mmol) of Z-Lys(Boc)-N-(3-pyridylmethyl) amide are dissolved in 20 ml of TFA at 0° C. and the solution is stirred for 20 min. The excess TFA is concentrated and the oily residue is treated with 10 ml of DMF. 4.6 ml (42.5 mmol) of N-methylmorpholine, 1.15 g (4.25 mmol) of 4-[[4-aminoiminomethyl)phenyl]amino]-4-oxobutyric acid hydrochloride, 2.35 g (5.3 mmol) of BOP and 20 ml of DMF are then added. The mixture is stirred at room temperature for 24 hours. The DMF is concentrated, and the residue is digested twice with 40 ml of water, then filtered off with suction and dried. The crude product is purified by chromatography on a silica gel column using the eluent 89b (70% HCCl$_3$, 40% MeOH, 10% CH$_3$COO$^-$Na$^{+\ in}$ 1 Mol per liter NH$_4$OH 25%). Yield: 340 mg (14% of theory).

Examples 36 to 55 were obtained analogueously to Example 35.

TABLE 4

Melting points of the compounds according to Examples 35 to 55

| Example | m.p. [°C.] |
|---------|-----------|
| 31 | 190–198 |
| 32 | 218–220 |
| 33 | 209 |
| 34 | 195 |
| 35 | 189–191 |
| 36 | 215–220 |
| 37 | 183 |
| 38 | 190 |
| 39 | 198 |
| 40 | 213 |
| 41 | |
| 42 | 175 |
| 43 | 196 |
| 44 | 217 |
| 45 | 189 |
| 46 | 197 |
| 47 | |
| 48 | |
| 49 | |
| 50 | 194 |
| 51 | |

Further compounds of the general Formula I were prepared according to the following Schemes 4 and 5.

Scheme 4: Reaction with carboxylic acids

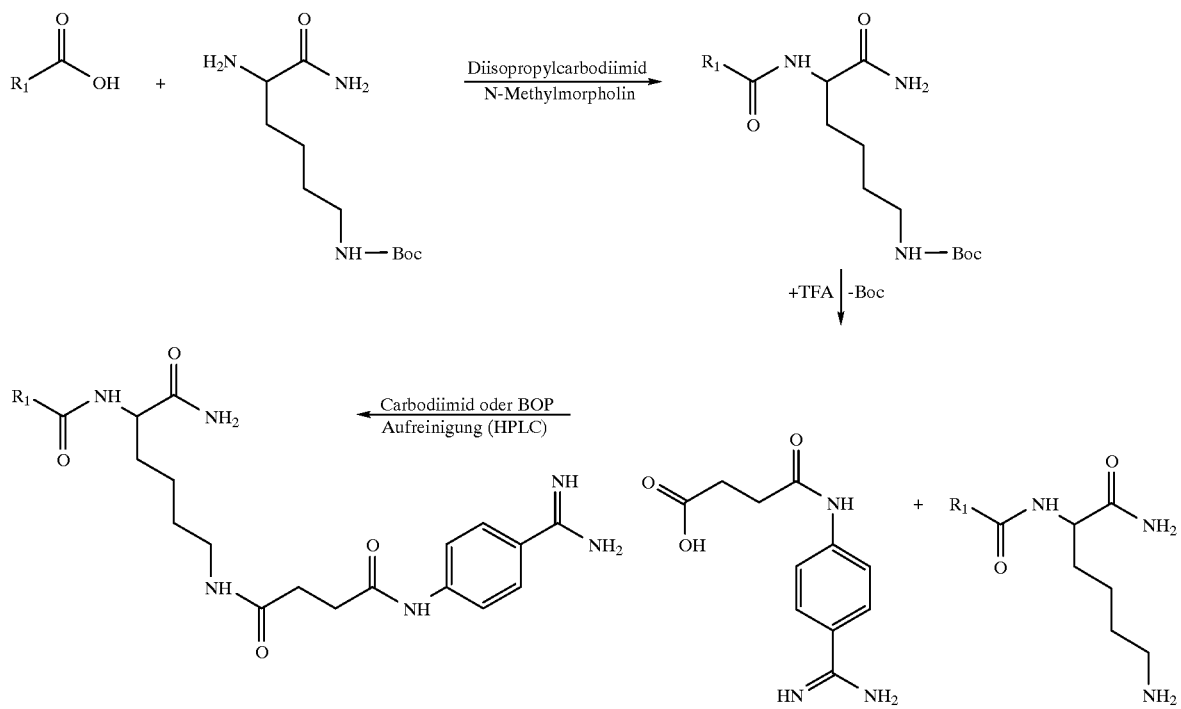

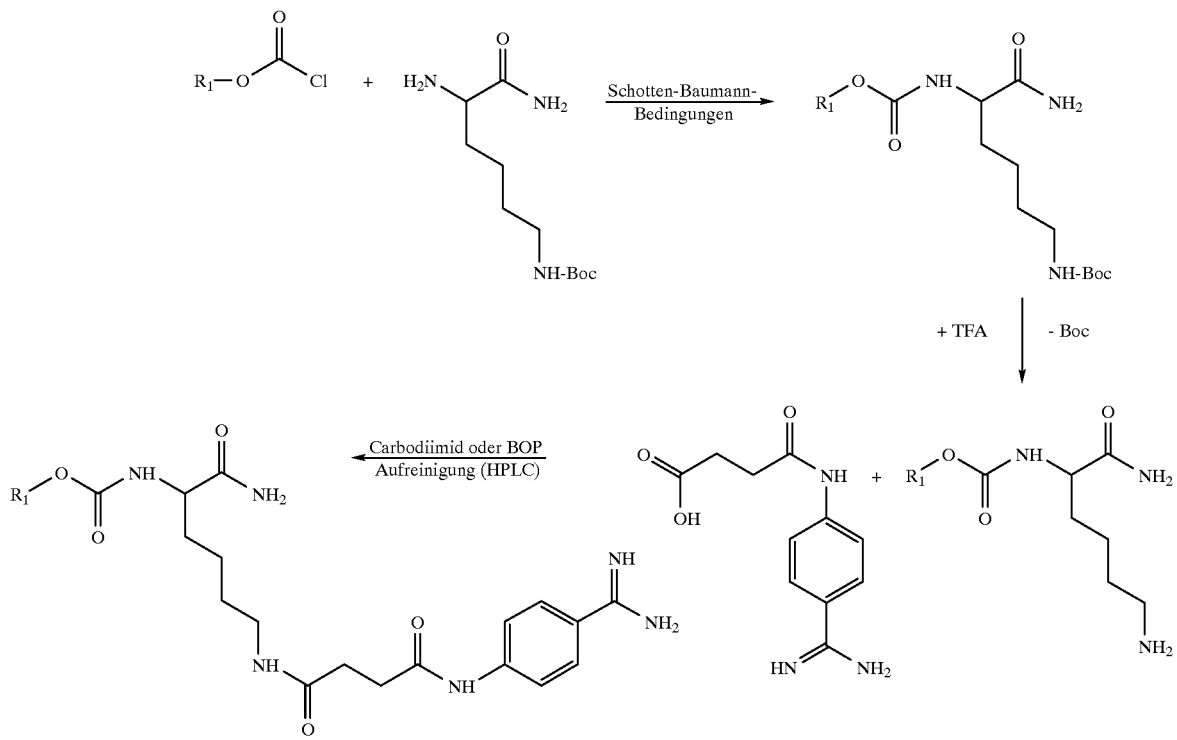

Scheme 5: Reaction with chloroformic acid esters

1. Acylation with carboxylic acids or chloroformic acid esters according to Schemes 4 and 5:

H-Lys(Boc)-NH₂ is reacted at room temperature in an aprotic solvent (DMF, DMSO) in the presence of a base (DIPEA, NMM) and of a coupling reagent (DCC, DIC, EDCI) with a carboxylic acid to give the resulting amide. After removal of the solvent, the residue is treated with water and the poorly soluble crude product is filtered off with suction. The product can be purified by crystallization from alcohol (MeOH, EtOH<2-PrOH) or esters (MEK, EA).

The reaction of H-Lys(Boc)-NH₂ with carbonyl chlorides in aqueous-alkaline solution (Schotten-Baumann conditions) leads to the desired derivatives in 90–95% yields. The crude product is isilated by filtering off with suction and purified by recrystallization from alcohol (MeOH/EtOH/isopropanol) or ethyl acetate or methyl ethyl ketone.

2. Removal of the Boc protective group using TFA:

The removal of the Boc protective group at room temperature in a mixture of dichloromethane and trifluoroacetic acid (2:1) is quantitative after approximately 60 min. The isolated, usually oily crude product R₁-Lys-NH₂ is rapidly further reacted without further purification steps.

3. Acylation where R₄=4-((4-(aminoiminomethyl)phenyl)amino)-4-oxobutyric acid hydrochloride:

The reaction with a further carboxylic acid (R₄) is carried out in aprotic solvents (DMF, DMSO) at room temperature in the presence of a base (NMM, DIPEA) using coupling reagents such as EDCI, Bop or PyBop. After removing the solvents, the product precipitates on addition of water. Purification is carried out by means of preparative HPLC on an RP₁₈₋ column using eluent mixtures of water, acetonitrile and trifluoroacetic acid. The product is obtained as the TFA salt.

According to this general procedure, on which the Synthesis Schemes 4 and 5 are based, compounds were synthesized which follow below from the description of Example 56 and the following Table 5:

EXAMPLE 56

32 mmol of Z-lysinamide hydrochloride and 32 mmol of 4-((4-(aminoiminomethyl)phenyl)amino)-4-oxybutyric acid hydrochloride are added at room temperature to 120 ml of dry, degassed N,N-dimethylformamide (DMF).

The starting materials dissolve rapidly with stirring; after addition of 104 mmol of diisopropylethylamine and 40 mmol of BOP the mixture is stirred at RT for 16 h.

Solvent and excess DIPEA are stripped of on a rotary evaporator at a bath temperature of 50–55° C. and about 10 mbar. The oily residue is treated with 250 ml of water, homogenized in an ultrasonic bath and cooled. Precipitated crude product is filtered off with suction and washed with water on the suction filter.

After drying in vacuo over calcium chloride, about 16 g of beige powder having a purity of about 90% (HPLC) are obtained as the HCl salt.

To prepare the corresponding trifluoroacetate, the product is suspended in 100 ml of water and treated with 32 mmol (2.45 ml) of trifluoroacetic acid (99%). In order to remove excess acid again, the mixture is evacuated briefly on a rotary evaporator, then the aqueous suspension is lyophilized.

After recrystallization from alcohol (EtOH/MeOH), the product thus obtained can be lyophilized again for better solubility.

Yield: 5.26 g

M.p.: 210–213° C.

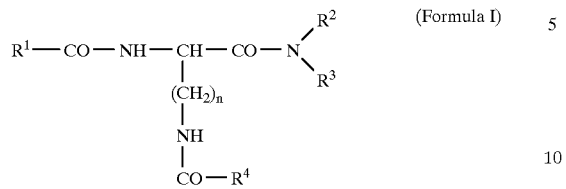

(Formula I)

TABLE 5

α,ε-N-substituted L-lysinamide derivatives according to Schemes 4 and 5 and of the general formula I (for all Examples n is equal to 4)

| Example | R¹—CO | R²/R³ | R⁴ |
|---|---|---|---|
| 56 | ![benzyloxycarbonyl] | H/H | ![propionamido-benzamidine] |
| 57 | ![3-phenylpropanal] | | |
| 58 | ![3-(4-fluorophenyl)propanal] | | |
| 59 | ![2-naphthylacetaldehyde] | | |
| 60 | ![quinolinyl-methoxy-chloro-benzaldehyde] | H/H | ![propionamido-benzamidine] |
| 61 | ![6-methoxy-naphthyl-propanal] | | |
| 62 | ![4-(2-naphthyl)butanal] | | |

TABLE 5-continued

α,ε-N-substituted L-lysinamide derivatives
according to Schemes 4 and 5 and of the general formula
I (for all Examples n is equal to 4)

| Example | R¹—CO | R²/R³ | R⁴ |
|---|---|---|---|
| 63 | [4-oxo-4-(phenanthren-1-yl)butanal] | | |
| 64 | [biphenyl-4-carbaldehyde] | | |
| 65 | [4-benzoylbenzaldehyde] | | |
| 66 | [9H-fluorene-9-carbaldehyde] | | |
| 67 | [2-(9H-fluoren-9-yl)acetaldehyde] | | |
| 68 | [2,2-diphenylacetaldehyde] | | |
| 69 | [3-(3,4,5-trimethoxyphenyl)propanal] | H/H | [N-(4-carbamimidoylphenyl)propanamide] |
| 70 | [phenyl formate] | | |

TABLE 5-continued

α,ε-N-substituted L-lysinamide derivatives
according to Schemes 4 and 5 and of the general formula
I (for all Examples n is equal to 4)

| Example | $R^1$—CO | $R^2/R^3$ | $R^4$ |
|---|---|---|---|
| 71 | 4-nitrophenyl formate | | |
| 72 | isobutyl formate | | |
| 73 | benzaldehyde | | |
| 74 | 9-fluorenylmethyl formate | | |
| 75 | tert-butyl formate | | |
| 76 | 2-ethylhexyl formate | | |
| 77 | phthalaldehyde | | |
| 78 | ethyl formate | | |
| 79 | propyl formate | H/H | N-(4-amidinophenyl)propanamide |
| 80 | 2-chloroethyl formate | | |
| 81 | tetradecyl formate | | |

TABLE 5-continued

α,ε-N-substituted L-lysinamide derivatives
according to Schemes 4 and 5 and of the general formula
I (for all Examples n is equal to 4)

| Example | R¹—CO | R²/R³ | R⁴ |
|---|---|---|---|
| 82 | (long-chain alkyl-O-CHO structure) | | |

TABLE 6

Melting points of the compounds according to
Examples 56 to 82

| Example | m.p. [°C.] |
|---|---|
| 56 | 210–213 |
| 57 | 220–223 |
| 58 | 213–215 |
| 59 | 223–226 |
| 60 | up to 233 |
| 61 | up to 237 |
| 62 | up to 221 |
| 63 | up to 220 |
| 64 | 230–236 |
| 65 | 218–222 |
| 66 | 216–219 |
| 67 | 235–238 |
| 68 | up to 218 |
| 69 | 205–208 |
| 70 | 168–170 |
| 71 | 197–202 |
| 72 | 221–226 |
| 73 | 225–228 |
| 74 | 191–193 |
| 75 | 186–188 |
| 76 | 220–222 |
| 77 | 210–215 |
| 78 | up to 223 |
| 79 | up to 226 |
| 80 | 194–197 |
| 81 | 215–222 |
| 82 | 219–222 |

Note: The statement "up to . . ." indicates that the substance formed an amorphous foam having corresponding physical properties after freeze-drying. A melting point in the strict sense did not exist, but rather a slow sintering together until liquefaction.

Salts of the compounds of the general Formula I

The compounds according to the invention can also be present as acid addition salts, for example as salts of mineral acids, such as, for example, hydrochloric acid, sulphuric acid, phosphoric acid, salts of organic acids, such as, for example, acetic acid, trifluoroacetic acid, lactic acid, malonic acid, maleic acid, fumaric acid, gluconic acid, glucuronic acid, citric acid, embonic acid, methanesulphonic acid, hydroxyethanesulphonic acid, pyruvic acid and succinic acid.

Both the compounds of the general formula I and their salts are biologically active. The compounds of the general formula I can be administered in free form or as salts with a physiologically tolerable acid. Administration can be carried out orally, parenterally, intravenously, transdermally or by inhalation.

The invention furthermore relates to pharmaceutical preparations containing at least one compound of the formula I or its salt with physiologically tolerable inorganic or organic acids and, if appropriate, pharmaceutically utilizable excipients and/or diluents or auxilaries.

EXAMPLE 83

Binding affinities of Cetrorelix, Example 1, Example 2 and Example 56 to the human LH-RH receptor (Cetrorelix: Ac-D-Nal(2)-D-p-Cl-Phe-D-Pal(3)-Ser-Tyr-D-Cit-Leu-Arg-Pro-D-Ala-$NH_2$)

Method for the determination of the binding affinity (dissociation constant Kd):

The binding affinity was determined by a competitive binding test ("displacement binding experiment"; Beckers et al. Eur. J. Biochem. 231, 535–543, 1995). The radiolabelled ligand used is [$^{125}$I] Cetrorelix (specific activity 5–10×$10^5$ dpm/pmol; dissolved in 20% v:v acetonitrile, 0.2% w:v albumin, 0.1% w:v TFA, ~80% v:v aqua). The binding ability of the iodinated peptide is between 60% and 85%. The non-labelled test compounds used are Cetrorelix, Example 1, Example 2 and Example 5 in solution. The substances are employed in concentrations of 0.01 nM–1000 nM (Cetrorelix, Example 1, Example 2) or 0.01 μM–10 μM (Example 56).

The cells of the individual cell clone L3.5/78 verexpressing the human LH-RH receptor which are used for the binding test are removed with PBS/EDTA (PBS without $Ca^{2+}$/$Mg^{2+}$/1 mM EDTA) from a cell culture dish grown under non-confluent conditions, the cell count is determined and the cells are resuspended in incubation medium (Dulbecco's modified Eagle Medium with 4.5 g/l glucose, 10 mM Hepes pH 7.5, 0.5% w:v BSA, 1 g/l bacitracin, 0.1 g/l SBTI, 0.1% w:v $NaN_3$) at a corresponding cell density. 200 μl of silicone/paraffin oil mixture (84/16% by volume) are initially introduced into special 400 μl reaction vessels (Renner, Beckman type) and 50 μl of the cell suspension (2.5×$10^5$ cells) are pipetted onto it. 50 μl of binding medium containing [$^{125}$I] Cetrorelix and the compound to be tested at the appropriate concentration are added to the cell suspension on the silicone/paraffin oil layer. The mixture is then incubated with rotation for 60 min at 37° C. in a warm cabinet. After this step, it is centrifuged at 9000 rpm (room temperature) for 2 min in the Heraeus Biofuge 15 in the HTA 13.8 rotor. In the course of this, the cells pelletize through the silicone/paraffin oil layer and are thus separated from the binding medium. After centrifugation, the reaction vessels are shock-frozen in liquid $N_2$ and the tip of the reaction vessel (cell pellet) is cut off with a pair of pincers and the tip containing the cell pellet (bound ligand [$^{125}$I] Cetrorelix) and the supernatant (unbound, free ligand [$^{125}$I] Cetrorelix) are transferred to counting tubes. To determine the maximum binding (Bo), no competitor is added. For the determination of non-specific binding, 1 μM unlabelled Cetrorelix is added for competition. At ≦10% of the total binding Bo, the non-specific binding is low. Quantification is carried out in a γ-counter; analysis is carried out using the EBDA/ligand V3.0 programme (McPherson, J. Pharmacol. Methods 14, 213–228, 1985). Plotting in the dose-response graph makes possible the estimation of the $IC_{50}$ (concentration which causes 50% inhibition of the reaction at the receptor) and the EBDA/ligand programme calculates the dissociation constant Kd [nM] from this.

Result: from the competition curves (see FIG. 1) it is evident that all compounds tested compete with the radio-labelled ligand [$^{125}$I] Cetrorelix) for binding to human LH-RH receptor. In each case, the binding (in % of the total binding Bo) is plotted against the concentration of the competitor. For the compounds shown in FIG. 1, it was possible to calculate the following binding affinities as the dissociation constant Kd [nM]: Cetrorelix (SB-75)—0.214 nM, Example 1—0.305 nM, Example 2—0.104 nM and Example 56—986 nM. The binding affinities as the mean value of various determinations can be taken from Table 7.

EXAMPLE 84

Antagonistic action of Example 2 and Example 56 in the functional assay on the human LH-RH receptor Method for the determination of IP3 (D-myo-1,3,5-triphosphate): a subconfluent culture of the cell clone (L 3.5/78) overexpressing the human LH-RH receptor is washed 1× with PBS, the cells are removed with PBS/EDTA and the cell suspension is pelletted. The cells are resuspended in incubation medium (Dulbecco's modified Eagle Medium with 4.5 g/l of glucose, 10 mM Hepes pH 7.5, 0.5% w:v BSA, 5 mM of LiCl, 1 g/l of bacitracin, 0.1 g/l of SBTI), aliquoted into 1.5 ml reaction vessels and preincubated at 37° C. for 30 min. $4 \times 10^6$ cells in a 500 μl volume are needed per measuring point. After the preincubation step, LH-RH (stock solution 0.5 mM in 10 mM tris pH 7.5, 1 mM dithiothreitol, 0.1% w:v BSA/Bachem Art # H4005) are added to the cell suspension at a final concentration of 10 nM. The action of an antagonist is tested by simultaneous addition at the corresponding concentration (for example 0.0316, 0.1, 0.316 etc. up to 100 nM for Example 2). As a negative control, cells without added LH-RH are incubated. After incubation at 37° C. for 15 min, $IP_3$ formed is isolated from the cells by means of trichloroacetic acid (TCA) extraction. To this end, 500 μl of ice-cold 15% (w:v) TCA solution are added to the cell suspension. The resulting precipitate is pelletted by centrifugation at 40° C. in the Heraeus Biofuge 15R centrifuge at 2000×g for 15 min. The supernatant of 950 μl is extracted 3× with 10 vol of cold, water-saturated diethyl ether in a 15 ml vessel standing on ice. After the last extraction step, the solution is adjusted to a pH of 7.5 with 0.5 M $NaHCO_3$ solution.

The determination of the $IP_3$ concentration in the cell extracts is carried out by means of a sensitive competitive binding test using an $IP_3$ binding protein, labelled [$^3$H]-$IP_3$ and unlabelled $IP_3$. To this end, an assay kit from Amersham (TRK 1000) is used; the determination is carried out as described in the assay protocol. After carrying out the various steps, 2 ml of scintillator for aqueous samples (Rotiszint Ecoplus) is finally added, the resuspended pellet containing the bound [$^3$H]-$IP_3$ is carefully mixed with it, and measured in a β-scintillation counter. The amount of cellular $IP_3$ is calculated using a standard curve and a dose-response curve is set up. The $IC_{50}$ can be estimated from the inflection point of this curve.

Figure 2:
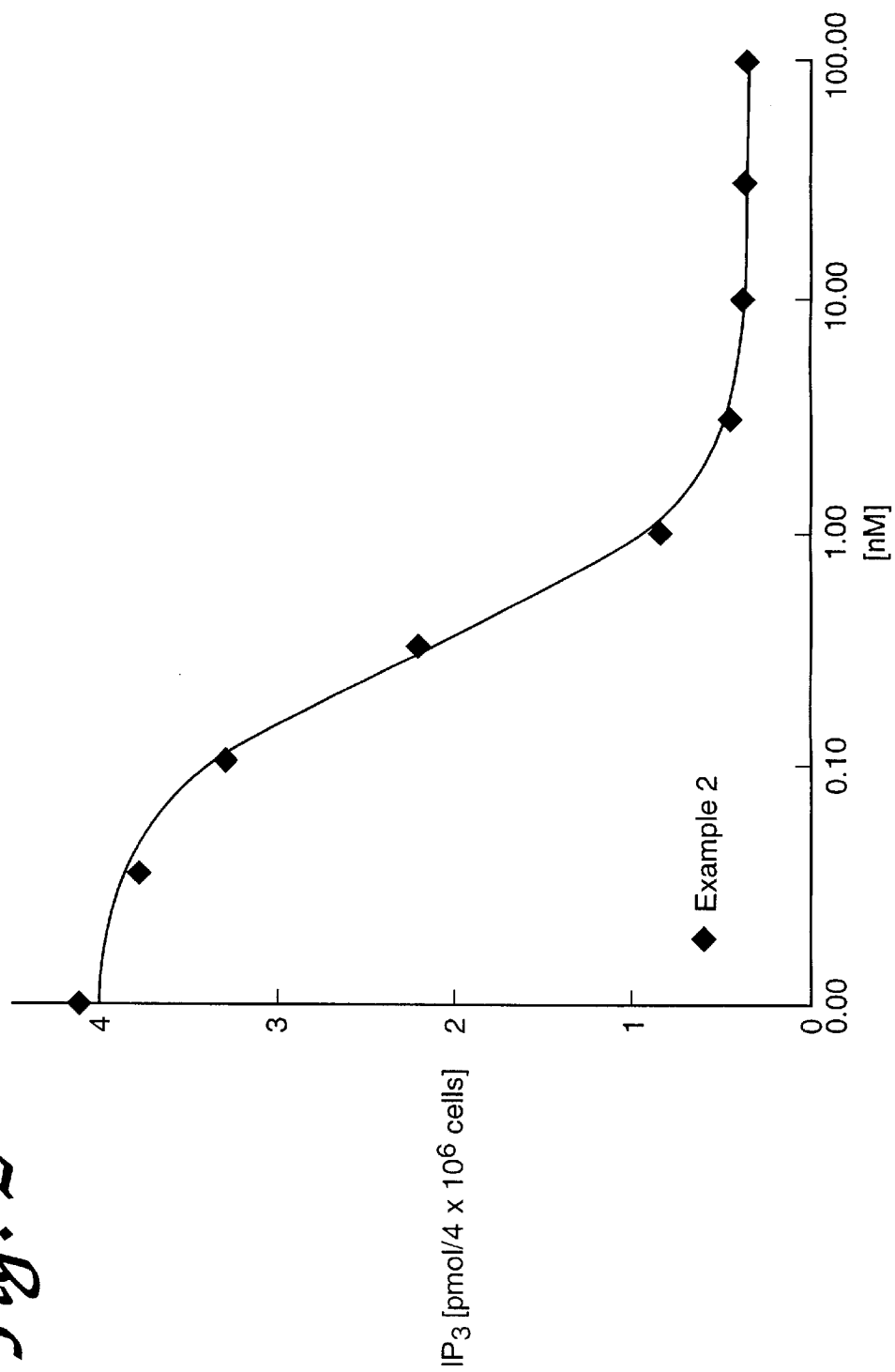
Figure 3:
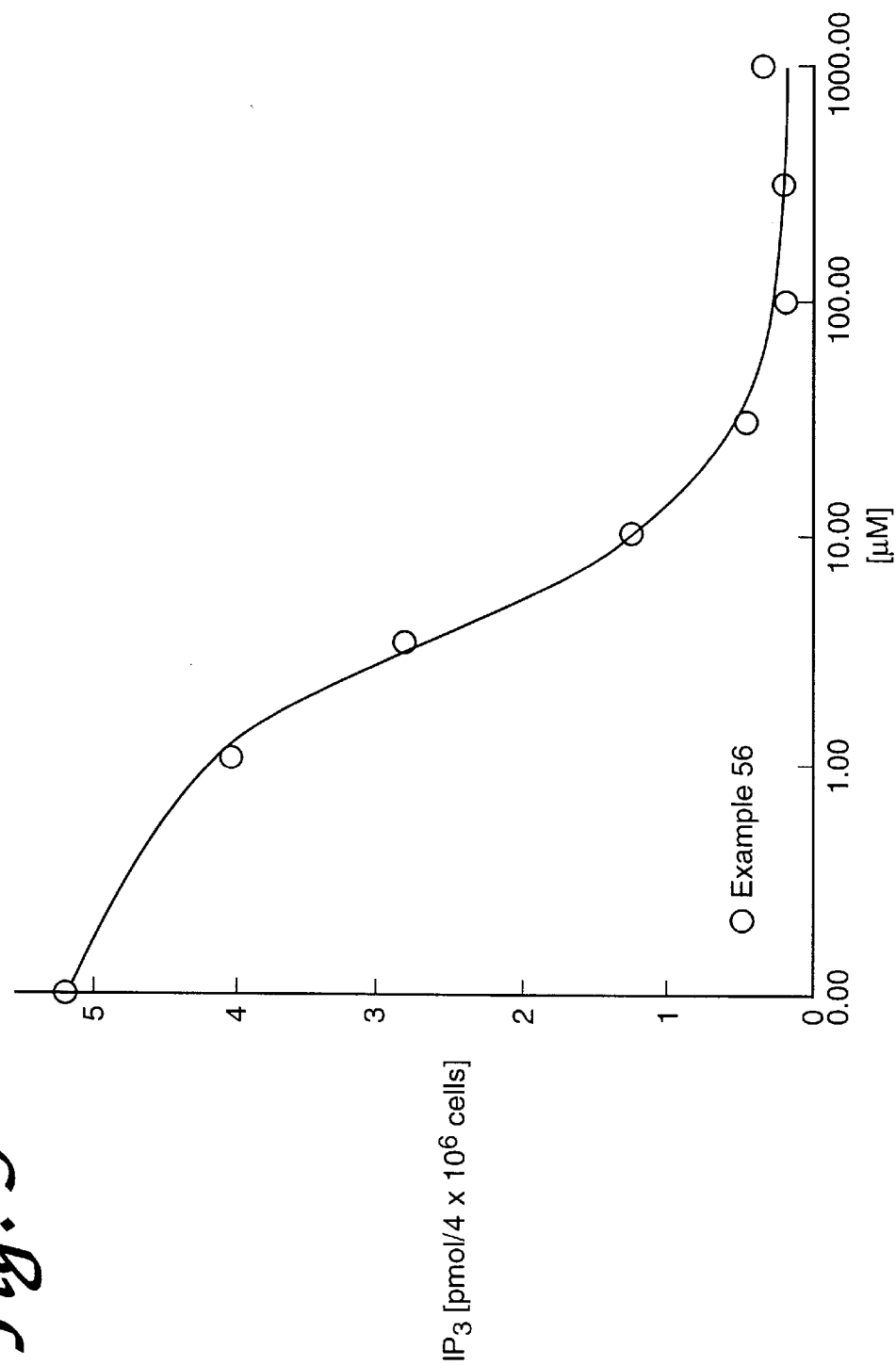

Result: FIG. 1 shows appropriate dose-response curves for the peptide antagonists Example 2 (FIG. 2), as well as for the peptidomimetic Example 56 (FIG. 3). Stimulation was carried out with 10 nM LH-RH and the inhibition of formation of $IP_3$ determined as a function of the substance concentration. For Example 2 and Example 56, it was not possible to determine any agonistic activity, i.e. the substances by themselves do not lead to any stimulation of $IP_3$ synthesis. In control experiments not presented here, it was shown that non-transfected cells cannot be stimulated by LH-RH to $IP_3$ synthesis. The $IP_3$ concentrations still measurable at the highest concentrations correspond to those of unstimulated cells. In Example 2 and Example 56 we are thus dealing with functional antagonists of LH-RH. The substances differ, however, in their potency. Under the experimental conditions selected, the $IC_{50}$ of Example 2 is approximately 0.4 nM, the $IC_{50}$ for Example 56, however, is approximately 4 μM. These activities correlate very well with the in vitro binding affinities, determined in the competitive binding test using [$^{125}$I]-Cetrorelix, of Kd=0.109 nM for Example 2 and Kd=1.08 μM for Example 56.

EXAMPLE 85

Figure 4:
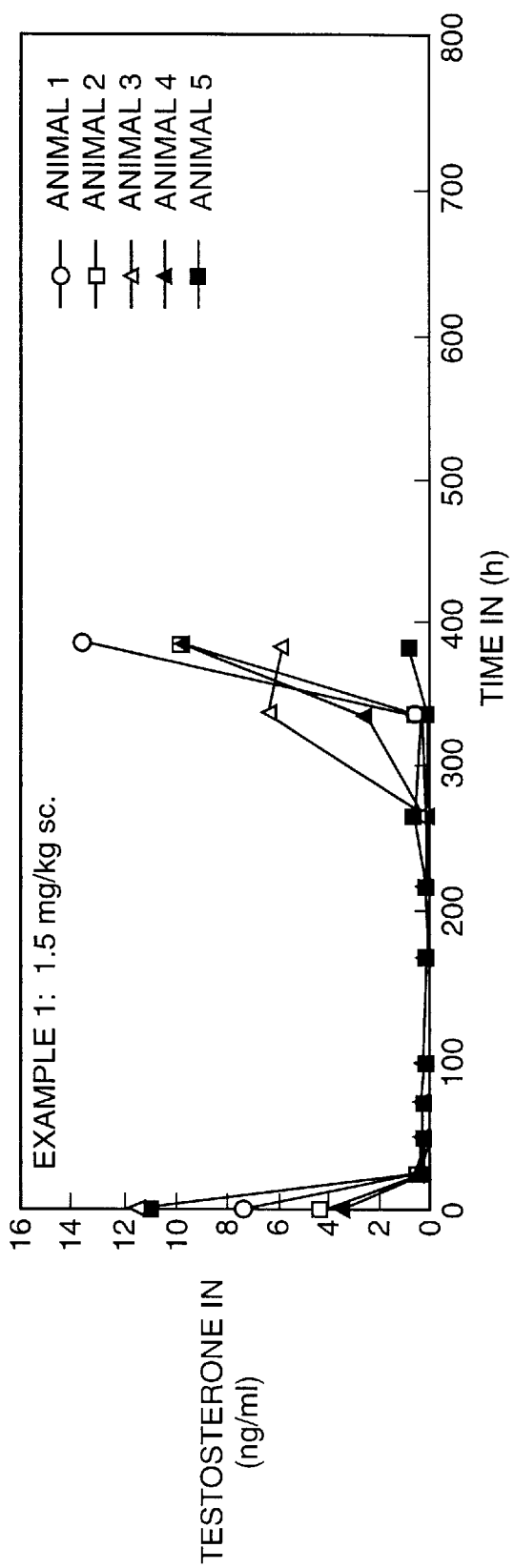
Figure 5:
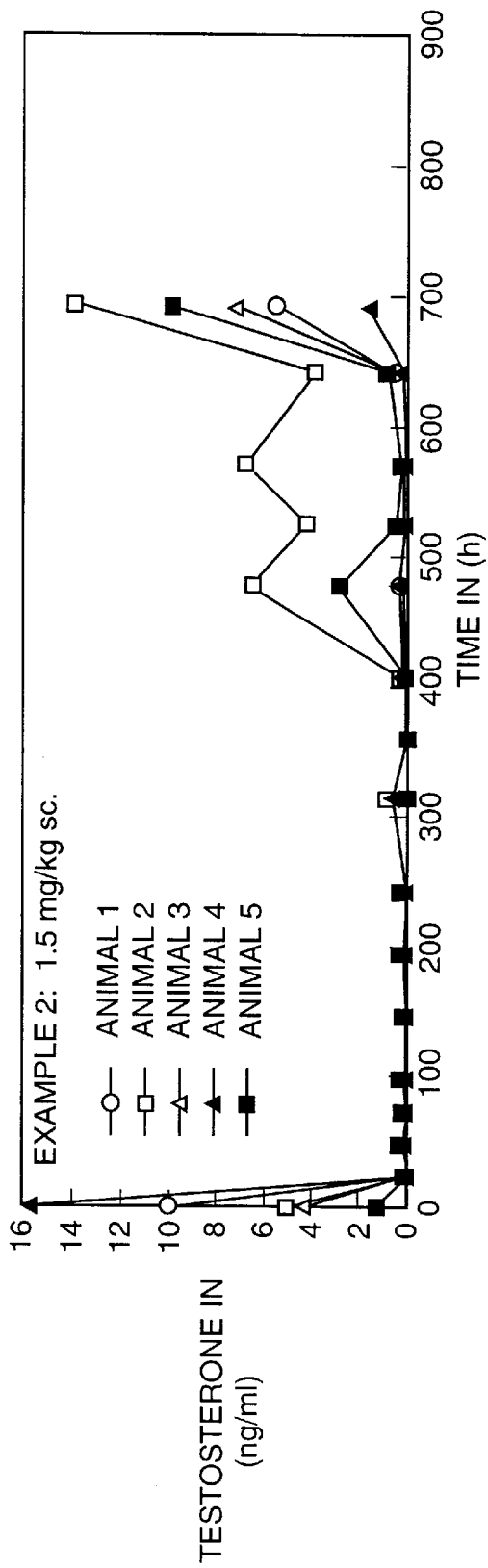
Figure 6:
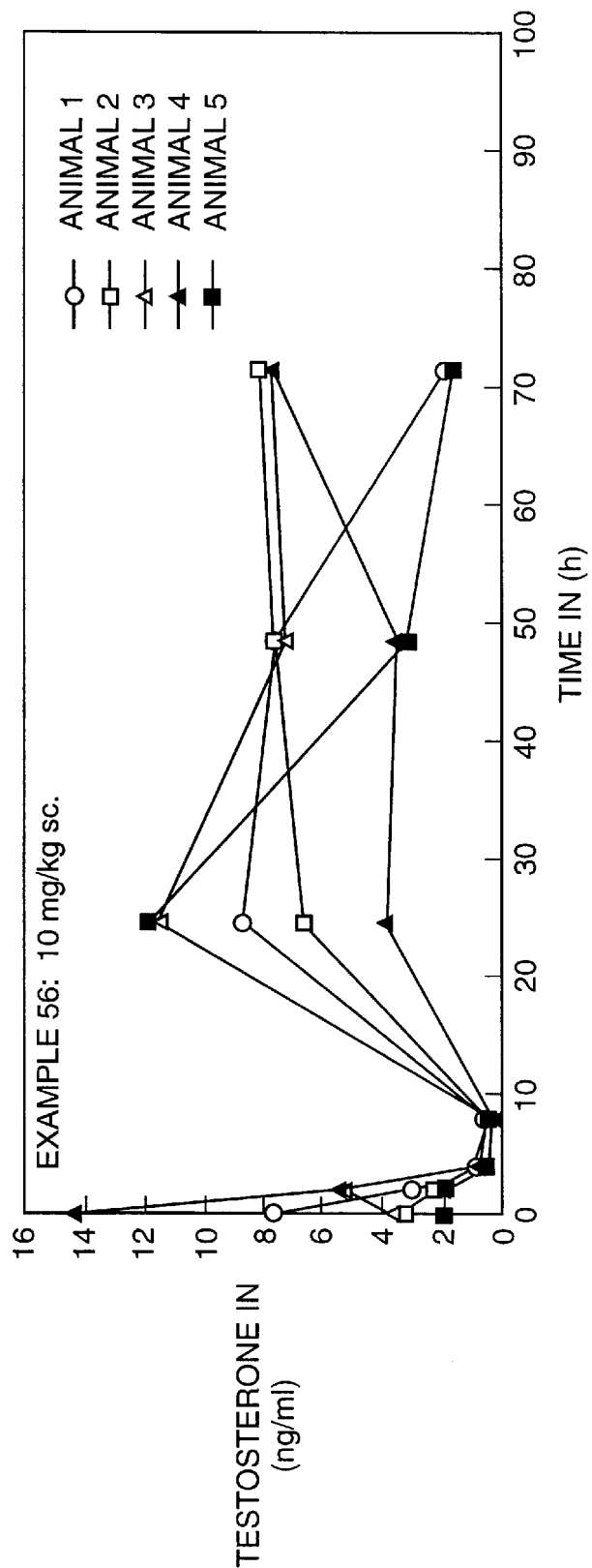

Hormone-suppressive action of Example 1, Example 2 and Example 56 in the healthy male rat To determine the suppression of testosterone in the blood of healthy male rats, the substance was injected subcutaneously into the right flank of the animals. The dosage was 1.5 mg/kg in the case of Example 1 and Example 2 and 10 mg/kg in the case of Example 56. To check the testosterone values, about 300 μl of blood were taken from the animals from the sublingual vein at the times 0, 2, 4, 8 (only Example 56), 24, 48, 72 and 96 hours, and then every 3 days until the end of suppression. Suppression with 1 ng/ml of testosterone after the administration of Example 1 lasted up to 264 hours in one animal, up to 336 hours in two animals and up to 384 hours in one animal (FIG. 4). After administration of Example 2, the testosterone level in one animal was suppressed for up to 408 hours, and in four animals for up to 648 hours (FIG. 5). Example 56 (10 mg/kg s.c.) suppressed the testosterone level in all 5 animals even after 2 hours and maintained this action for up to 8 hours. At the next measuring point (24 h), the testosterone values rose again (FIG. 6).

TABLE 7

Biological data
Binding affinities to human LH-RH receptor (expressed as the dissociation constant Kd [nM]; evaluation using the EBDA/Ligand Analysis Programme. Mean values from various experiments are indicated, number of experiments in brackets) as well as testosterone suppression in vivo, histamine release in vitro and water solubility in comparison to SB-75:

| Substance | Affinity human LH-RH receptor [nmol/L] | (1.5 mg/kg, single dose) testosterone suppression rats [h] | ($IC_{50}$) Histamine releage [μg/ml] | $H_2O$ Solubility [mg/ml] |
|---|---|---|---|---|
| Cetrorelix SB-75 | 0.202 (10) | 144 | 9.7 | 9 |
| Example 1 | 0.306 (2) | 336 | 31.9 | 27 |
| Example 2 | 0.109 (2) | 648 | 17.1 | 23 |
| Example 3 | 0.170 (2) | 864 | n.d.* | n.d. |
| Example 4 | 0.206 (2) | 696 | n.d. | n.d. |
| Example 56 | 1082 (2) | — | — | — |

*)Not determinable because of poor solubility

We claim:

1. Compound of the general formula I

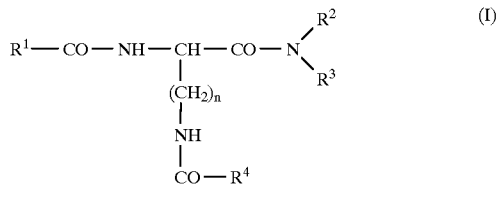 (I)

in which n is the number 3 or 4, $R^1$ is an alkyl group, an alkyloxy group, an aryl group, a heteroaryl group, an aralkyl group, a heteroaralkyl group, an aralkyloxy group or a heteroaralkyloxy group, in each case unsubstituted or substituted, $R^2$ and $R^3$ independently of one another are each a hydrogen atom, an alkyl group, an aralkyl group or a heteroaralkyl group, in each case unsubstituted or substituted, where the substitution can in turn consist of an aryl group or heteroaryl group, or $-NR^2R^3$ is an amino acid group, and $R^4$ is a group having the formula (II)

 (II)

in which p is an integer from 1 to 4, $R^5$ is hydrogen or an alkyl group and $R^6$ is an unsubstituted or substituted aryl or heteroararyl group, or $R^4$ is a ring of the general formula (III)

 (III)

in which q is the number 1 or 2, $R^7$ is a hydrogen atom or an alkyl group, $R^8$ is a hydrogen atom or an alkyl group and X is an oxygen or sulphur atom, where the aromatic or heteroaromatic radicals can be partially or completely hydrogenated and chiral carbon atoms can have the R- or S-configuration, and its salts with pharmaceutically acceptable acids.

2. α-N-Z-[ε-N'-4-(4-Amidinophenyl)amino-1,4-dioxobutyl]lysinamide and its salts with pharmaceutically acceptable acids.

3. α-N-Z-[E-N'-4-(4-Amidinophenyl)amino-1,5-dioxopentyl]lysinamide and its salts with pharmaceutically acceptable acids.

4. α-N-Z-[E-N'-(Imidazolidin-2-on-4-yl)-formyl]lysinamide and its salts with pharmaceutically acceptable acids.

5. Compound according to claim 1, in which the salt is an embonate.

6. Compound of the general formula V

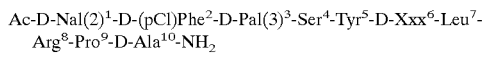

in which D-Xxx is an amino acid group of the general formula (VI)

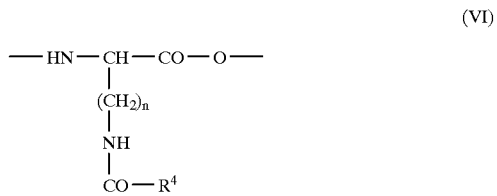 (VI)

in which n is the number 3 or 4, $R^4$ is a group of the formula (II)

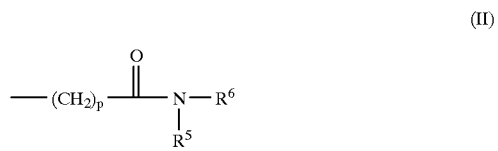 (II)

in which p is an integer from 1 to 4, $R^5$ is hydrogen or an alkyl group and $R^6$ is an unsubstituted or substituted aryl group or heteroaryl group, or $R^4$ is a ring of the general formula (III)

 (III)

in which q is the number 1 or 2, $R^7$ is a hydrogen atom or an alkyl group, $R^8$ is a hydrogen atom or an alkyl group and X is an oxygen or sulphur atom, and its salts with pharmaceutically acceptable acids.

7. Compound according to claim 6, in which Xxx is a [ε-N-4-(4-amidinophenyl)amino-1,4-dioxobutyl]lysyl group.

8. Compound according to claim 6, in which Xxx is a [ε-(imidazolidin-2-on-4-yl)formyl]lysyl group.

9. Compound according to claim 6, in which the salt is an embonate.

10. Pharmaceutical composition comprising a compound according to claim 1 or 6.

11. Process for the preparation of a compound according to claim 6, comprising the steps of
   (a) providing the α-amino and the carboxylic acid group of D-lysine or D-ornithine with suitable protective groups,
   (b) reacting the D-lysine or D-ornithine provided with protective groups with a carboxylic acid of the general formula (VII)

in which $R^4$ is as defined in claim 1,
   (c) removing the protective group on the α-carboxylic acid group of the compound obtained in step (b) for the purpose of incorporation in pos. 6 in step (h),
   (d) coupling of D-alanine provided on the amino group with a protective group to a solid support in the form of a resin, (e) removing the protective group on the amino group of the alanine, (f) reacting the alanine bound to the solid support with proline which is provided with a protective group on the nitrogen atom, (g) removing the protective group on the nitrogen atom of the proline, (h) repeating steps f) and g) with the amino acids 1 to 8 according to the general formula (V), in the sequence from 8 to 1, using modified D-lysine or D-ornithine described in step (c) for pos. 6, (i) removing the compound obtained in step (h) from the support and, if appropriate, purifying, in particular by HPLC, (j) if desired, reacting with a pharmaceutically acceptable acid, preferably embonic acid.

12. Process for the preparation of a compound according to claim 6, comprising the steps of (a) coupling D-alanine provided with a protective group on the amino group to a support suitable for solid-phase synthesis, (b) removing the protective group on the amino group of the alanine, (c) reacting the alanine bound to the resin with proline which is provided with a protective group on the nitrogen atom, (d) removing the protective group on the nitrogen atom of the proline, (e) repeating steps c) and d) with the amino acids 1 to 8 according to the general formula (V), in the sequence from 8 to 1, (f) removing the compound obtained in step (e) from the support, (g) reacting with a carboxylic acid of the formula (VII)

$$R^4\text{—COOH} \qquad (VII)$$

in which $R^4$ is as defined in claim 1, (h) if desired, reacting with a pharmaceutically acceptable acid, preferably embonic acid.

13. Process for the preparation of a compound according to claim 6, comprising the steps of (a) coupling D-alanine provided with a protective group on the amino group to a support suitable for solid-phase synthesis, (b) removing the protective group on the amino group of the alanine, (c) reacting the alanine bound to the resin with proline which is provided with a protective group on the nitrogen atom, (d) removing the protective group on the nitrogen atom of the proline, (e) repeating steps c) and d) with the amino acids 6 to 8 according to the general formula (V), in the sequence from 8 to 6, (f) removing the ε-amino protective group from D-lysine or D-ornithine in pos. 6 and reacting with a carboxylic acid of the formula (VII),

$$R^4\text{—COOH} \qquad (VII)$$

in which $R^4$ is as defined in claim 1, (g) removing the protective group on the α-amino group of the D-lysine or D-ornithine, (h) repeating steps c) and d) with the amino acids 1 to 5 according to the general formula (IV), in the sequence from 5 to 1, (i) removing the compound obtained in step (h) from the resin and purifying it, in particular by HPLC, (j) if desired, reacting with a pharmaceutically acceptable acid, preferably embonic acid.

14. Process according to one of claims 11 to 13, in which N-(4-amidinophenyl)amino-4-oxobutyric acid is used as the carboxylic acid of the general formula (VII).

15. Process according to one of claims 11 to 13, in which imidazolidin-2-one-4-carboxylic acid is used as the carboxylic acid of the general formula (VII).

16. Method for the treatment of hormone-dependent tumours, in particular prostate carcinoma or breast cancer, and for non-malignant indications whose treatment necessitates LH-RH hormone suppression, wherein a substance of claim 1 or 6 is used.

* * * * *